United States Patent
Gaw et al.

(10) Patent No.: US 9,615,767 B2
(45) Date of Patent: Apr. 11, 2017

(54) FLUID LEVEL INDICATOR DETERMINATION

(75) Inventors: Richelle Leanne Gaw, Greenslopes (AU); Brian John Thomas, Hill End (AU)

(73) Assignee: IMPEDIMED LIMITED, Pinkenba, Queensland (AU)

( * ) Notice: Subject to any disclaimer, the term of this patent is extended or adjusted under 35 U.S.C. 154(b) by 547 days.

(21) Appl. No.: 13/503,833

(22) PCT Filed: Oct. 21, 2010

(86) PCT No.: PCT/AU2010/001399
§ 371 (c)(1),
(2), (4) Date: Aug. 3, 2012

(87) PCT Pub. No.: WO2011/050393
PCT Pub. Date: May 5, 2011

(65) Prior Publication Data
US 2013/0131538 A1  May 23, 2013

(30) Foreign Application Priority Data
Oct. 26, 2009 (AU) ............... 2009905220

(51) Int. Cl.
*A61B 5/053* (2006.01)
*A61B 5/00* (2006.01)

(52) U.S. Cl.
CPC .......... *A61B 5/0537* (2013.01); *A61B 5/4878* (2013.01); *A61B 5/7225* (2013.01)

(58) Field of Classification Search
None
See application file for complete search history.

(56) References Cited

U.S. PATENT DOCUMENTS

| 3,316,896 A | 5/1967 | Thomasset |
| 3,851,641 A | 12/1974 | Toole et al. |
| 3,866,600 A | 2/1975 | Rey |

(Continued)

FOREIGN PATENT DOCUMENTS

| CA | 2231038 | 11/1999 |
| CA | 2638958 | 6/2000 |

(Continued)

OTHER PUBLICATIONS

Ivorra, Antoni, et al., "Bioimpedance dispersion width as a parameter to monitor living tissues," Physiol. Meas. 26 (2005) S165-S173.*

(Continued)

*Primary Examiner* — Devin Henson
*Assistant Examiner* — Matthew Kremer
(74) *Attorney, Agent, or Firm* — Knobbe Martens Olson & Bear LLP

(57) ABSTRACT

A method for use in analyzing impedance measurements on a subject is described. The method can include, in a processing system, determining at least one impedance value at each of a number of frequencies, each impedance value representing the impedance of a segment of the subject, determining a dispersion parameter value indicative of a dispersion of the impedance values and, determining an indicator based at least on part on the dispersion parameter value.

21 Claims, 7 Drawing Sheets

(56) References Cited

U.S. PATENT DOCUMENTS

| | | |
|---|---|---|
| 3,868,165 A | 2/1975 | Gonser |
| 3,871,359 A | 3/1975 | Pacela |
| 4,008,712 A | 2/1977 | Nyboer |
| 4,034,854 A | 7/1977 | Bevilacqua |
| 4,082,087 A | 4/1978 | Howson |
| 4,121,575 A | 10/1978 | Mills et al. |
| 4,144,878 A | 3/1979 | Wheeler |
| RE30,101 E | 9/1979 | Kubicek et al. |
| 4,169,463 A | 10/1979 | Piquard |
| 4,184,486 A | 1/1980 | Papa |
| 4,233,987 A | 11/1980 | Feingold |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,638,807 A | 1/1987 | Ryder |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,832,608 A | 5/1989 | Kroll |
| 4,836,214 A | 6/1989 | Sramek |
| 4,890,630 A | 1/1990 | Kroll et al. |
| 4,895,163 A | 1/1990 | Libke et al. |
| 4,899,758 A | 2/1990 | Finkelstein et al. |
| 4,905,705 A | 3/1990 | Kizakevich et al. |
| 4,911,175 A | 3/1990 | Shizgal |
| 4,922,911 A | 5/1990 | Wada et al. |
| 4,924,875 A | 5/1990 | Chamoun |
| 4,942,880 A | 7/1990 | Slovák |
| 4,951,682 A | 8/1990 | Petre |
| 4,981,141 A | 1/1991 | Segalowitz |
| 5,020,541 A | 6/1991 | Marriott |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,101,828 A | 4/1992 | Welkowitz et al. |
| 5,143,079 A | 9/1992 | Frei et al. |
| 5,184,624 A | 2/1993 | Brown et al. |
| 5,197,479 A | 3/1993 | Hubelbank et al. |
| 5,199,432 A | 4/1993 | Quedens et al. |
| 5,233,982 A | 8/1993 | Kohl |
| 5,246,008 A | 9/1993 | Mueller |
| 5,272,624 A | 12/1993 | Gisser et al. |
| 5,280,429 A | 1/1994 | Withers |
| 5,282,840 A | 2/1994 | Hudrlik |
| 5,284,142 A | 2/1994 | Goble et al. |
| 5,305,192 A | 4/1994 | Bonte et al. |
| 5,309,917 A | 5/1994 | Wang et al. |
| 5,311,878 A | 5/1994 | Brown et al. |
| 5,335,667 A | 8/1994 | Cha et al. |
| 5,351,697 A | 10/1994 | Cheney et al. |
| 5,353,802 A | 10/1994 | Ollmar |
| 5,372,141 A | 12/1994 | Gallup et al. |
| 5,381,333 A | 1/1995 | Isaacson et al. |
| 5,390,110 A | 2/1995 | Cheney et al. |
| 5,415,164 A | 5/1995 | Faupel e |
| 5,421,345 A | 6/1995 | Lekholm et al. |
| 5,423,326 A | 6/1995 | Wang et al. |
| 5,427,113 A | 6/1995 | Hiroshi et al. |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,575,929 A | 11/1996 | Yu et al. |
| 5,588,429 A | 12/1996 | Isaacson et al. |
| 5,611,351 A | 3/1997 | Sato et al. |
| 5,615,689 A | 4/1997 | Kotler |
| 5,626,146 A | 5/1997 | Barber et al. |
| 5,704,355 A | 1/1998 | Bridges |
| 5,730,136 A | 3/1998 | Laufer et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A * | 9/1998 | Kun et al. .................... 600/547 |
| 5,810,742 A | 9/1998 | Pearlman |
| 5,876,353 A | 3/1999 | Riff |
| 5,919,142 A | 7/1999 | Boone et al. |
| 5,947,910 A | 9/1999 | Zimmet |
| 5,957,861 A | 9/1999 | Combs et al. |
| 5,964,703 A | 10/1999 | Goodman et al. |
| 5,994,956 A | 11/1999 | Concorso |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,101,413 A | 8/2000 | Olson et al. |
| 6,115,626 A | 9/2000 | Whayne et al. |
| 6,122,544 A | 9/2000 | Organ |
| 6,125,297 A | 9/2000 | Siconolfi |
| 6,129,666 A | 10/2000 | DeLuca et al. |
| 6,142,949 A | 11/2000 | Ubby |
| 6,151,523 A | 11/2000 | Ferrer et al. |
| 6,167,300 A | 12/2000 | Cherepenin et al. |
| 6,173,003 B1 | 1/2001 | Whikehart et al. |
| 6,228,022 B1 | 5/2001 | Friesem et al. |
| 6,228,033 B1 | 5/2001 | Koobi |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,253,100 B1 | 6/2001 | Zhdanov |
| 6,256,532 B1 | 7/2001 | Cha |
| 6,280,396 B1 | 8/2001 | Clark |
| 6,292,690 B1 | 9/2001 | Petrucelli et al. |
| 6,308,097 B1 | 10/2001 | Pearlman |
| 6,339,722 B1 | 1/2002 | Heethaar et al. |
| 6,354,996 B1 | 3/2002 | Drinan et al. |
| 6,376,023 B1 | 4/2002 | Mori |
| 6,432,045 B2 | 8/2002 | Lemperle et al. |
| 6,459,930 B1 | 10/2002 | Takehara et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,501,984 B1 | 12/2002 | Church et al. |
| 6,511,438 B2 | 1/2003 | Bernstein et al. |
| 6,512,949 B1 | 1/2003 | Combs et al. |
| 6,516,218 B1 | 2/2003 | Cheng et al. |
| 6,522,910 B1 | 2/2003 | Gregory |
| 6,532,384 B1 | 3/2003 | Fukuda |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,564,079 B1 | 5/2003 | Cory et al. |
| 6,569,160 B1 | 5/2003 | Goldin et al. |
| 6,584,348 B2 | 6/2003 | Glukhovsky |
| 6,602,201 B1 | 8/2003 | Hepp et al. |

(56) References Cited

U.S. PATENT DOCUMENTS

| | | |
|---|---|---|
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtk |
| 6,633,777 B2 | 10/2003 | Szopinski |
| 6,636,754 B1 | 10/2003 | Baura et al. |
| 6,643,543 B2 | 11/2003 | Takehara et al. |
| 6,658,296 B1 | 12/2003 | Wong et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,760,617 B2 | 7/2004 | Ward et al. |
| 6,763,263 B2 | 7/2004 | Gregory et al. |
| 6,768,921 B2 | 7/2004 | Organ et al. |
| 6,788,966 B2 | 9/2004 | Kenan et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,840,907 B1 | 1/2005 | Brydon |
| 6,845,264 B1 | 1/2005 | Skladnev et al. |
| 6,870,109 B1 | 3/2005 | Villarreal |
| 6,875,176 B2 | 4/2005 | Mourad et al. |
| 6,906,533 B1 | 6/2005 | Yoshida |
| 6,922,586 B2 | 7/2005 | Davies |
| 6,936,012 B2 | 8/2005 | Wells |
| 6,940,286 B2 | 9/2005 | Wang et al. |
| RE38,879 E | 11/2005 | Goodman et al. |
| 6,980,852 B2 | 12/2005 | Jersey-Willuhn et al. |
| 6,980,853 B2 | 12/2005 | Miyoshi et al. |
| 7,065,399 B2 | 6/2006 | Nakada |
| 7,079,889 B2 | 7/2006 | Nakada |
| 7,096,061 B2 | 8/2006 | Arad |
| 7,122,012 B2 | 10/2006 | Bouton et al. |
| 7,130,680 B2 | 10/2006 | Kodama et al. |
| 7,132,611 B2 | 11/2006 | Gregaard et al. |
| 7,148,701 B2 | 12/2006 | Park et al. |
| 7,149,573 B2 | 12/2006 | Wang |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,206,630 B1 | 4/2007 | Tarler |
| 7,212,852 B2 | 5/2007 | Smith et al. |
| 7,233,823 B2 | 6/2007 | Simond et al. |
| 7,251,524 B1 | 7/2007 | Hepp et al. |
| 7,288,943 B2 | 10/2007 | Matthiessen et al. |
| D557,809 S | 12/2007 | Neverov et al. |
| 7,313,435 B2 | 12/2007 | Nakada et al. |
| 7,317,161 B2 | 1/2008 | Fukuda |
| 7,336,992 B2 | 2/2008 | Shiokawa |
| 7,440,796 B2 | 10/2008 | Woo et al. |
| 7,457,660 B2 | 11/2008 | Smith et al. |
| 7,477,937 B2 | 1/2009 | Iijima et al. |
| 7,496,450 B2 | 2/2009 | Ortiz Alemn |
| 7,499,745 B2 | 3/2009 | Littrup et al. |
| D603,051 S | 10/2009 | Causevic et al. |
| 7,603,158 B2 | 10/2009 | Nachman |
| 7,603,171 B2 | 10/2009 | Eror et al. |
| 7,628,761 B2 | 12/2009 | Gozani et al. |
| 7,638,341 B2 | 12/2009 | Rubinsky et al. |
| 7,657,292 B2 | 2/2010 | Baker et al. |
| 7,660,617 B2 | 2/2010 | Davis |
| 7,706,872 B2 | 4/2010 | Min et al. |
| 7,711,418 B2 | 5/2010 | Garber et al. |
| 7,729,756 B2 | 6/2010 | Mertelmeier et al. |
| 7,733,224 B2 | 6/2010 | Tran |
| 7,749,013 B2 | 7/2010 | Sato et al. |
| 7,860,557 B2 | 12/2010 | Istvan et al. |
| 7,917,202 B2 | 3/2011 | Chamney et al. |
| D641,886 S | 7/2011 | Causevic et al. |
| 7,983,853 B2 | 7/2011 | Wang et al. |
| D647,208 S | 10/2011 | Rothman et al. |
| 8,055,335 B2 | 11/2011 | Stylos |
| 8,068,906 B2 | 11/2011 | Chetham |
| 8,172,762 B2 | 5/2012 | Robertson |
| 8,233,617 B2 | 7/2012 | Johnson et al. |
| 8,233,974 B2 | 7/2012 | Ward et al. |
| D669,186 S | 10/2012 | Gozani |
| D669,187 S | 10/2012 | Gozani |
| 8,285,356 B2 | 10/2012 | Bly et al. |
| D674,096 S | 1/2013 | Gaw et al. |
| 8,467,865 B2 | 6/2013 | Gregory et al. |
| 8,744,564 B2 | 6/2014 | Ward et al. |
| D718,458 S | 11/2014 | Vosch et al. |
| D719,660 S | 12/2014 | Vosch et al. |
| D728,801 S | 5/2015 | Machon et al. |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0021799 A1 | 9/2001 | Ohlsson et al. |
| 2001/0025139 A1 | 9/2001 | Pearlman |
| 2001/0051774 A1 | 12/2001 | Littrup et al. |
| 2002/0020138 A1 | 2/2002 | Walker et al. |
| 2002/0022773 A1 | 2/2002 | Drinan et al. |
| 2002/0022787 A1 | 2/2002 | Takehara et al. |
| 2002/0035334 A1 | 3/2002 | Meij et al. |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0106681 A1 | 8/2002 | Wexler et al. |
| 2002/0109621 A1 | 8/2002 | Khair et al. |
| 2002/0111559 A1 | 8/2002 | Kurata et al. |
| 2002/0123694 A1 | 9/2002 | Organ et al. |
| 2002/0138019 A1 | 9/2002 | Wexler et al. |
| 2002/0161311 A1 | 10/2002 | Ward et al. |
| 2002/0193689 A1 | 12/2002 | Bernstein et al. |
| 2002/0194419 A1 | 12/2002 | Rajput et al. |
| 2003/0004403 A1 | 1/2003 | Drinan et al. |
| 2003/0009111 A1 | 1/2003 | Cory et al. |
| 2003/0023184 A1 | 1/2003 | Pitts-Crick et al. |
| 2003/0028221 A1 | 2/2003 | Zhu et al. |
| 2003/0036713 A1 | 2/2003 | Bouton et al. |
| 2003/0050570 A1 | 3/2003 | Kodama et al. |
| 2003/0073916 A1 | 4/2003 | Yonce |
| 2003/0105410 A1 | 6/2003 | Pearlman |
| 2003/0105411 A1 | 6/2003 | Smallwood et al. |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0176808 A1 | 9/2003 | Masuo |
| 2003/0216661 A1 | 11/2003 | Davies |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0059220 A1 | 3/2004 | Mourad et al. |
| 2004/0059242 A1 | 3/2004 | Masuo et al. |
| 2004/0073127 A1 | 4/2004 | Istvan et al. |
| 2004/0073130 A1 | 4/2004 | Bohm et al. |
| 2004/0077944 A1 | 4/2004 | Steinberg et al. |
| 2004/0116819 A1 | 6/2004 | Alt |
| 2004/0127793 A1 | 7/2004 | Mendlein et al. |
| 2004/0158167 A1 | 8/2004 | Smith et al. |
| 2004/0167423 A1 | 8/2004 | Pillon et al. |
| 2004/0171961 A1 | 9/2004 | Smith et al. |
| 2004/0181163 A1 | 9/2004 | Wong et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0220632 A1 | 11/2004 | Burnes |
| 2004/0234113 A1 | 11/2004 | Miga |
| 2004/0236202 A1 | 11/2004 | Burton |
| 2004/0242987 A1 | 12/2004 | Liew et al. |
| 2004/0242989 A1 | 12/2004 | Zhu et al. |
| 2004/0243018 A1 | 12/2004 | Organ et al. |
| 2004/0252870 A1 | 12/2004 | Reeves et al. |
| 2004/0253652 A1 | 12/2004 | Davies |
| 2004/0260167 A1 | 12/2004 | Leonhardt |
| 2004/0267333 A1 | 12/2004 | Kronberg |
| 2004/0267344 A1 | 12/2004 | Stett et al. |

(56) References Cited

U.S. PATENT DOCUMENTS

| | | |
|---|---|---|
| 2005/0033281 A1 | 2/2005 | Bowman et al. |
| 2005/0039763 A1 | 2/2005 | Kraemer et al. |
| 2005/0049474 A1 | 3/2005 | Kellogg et al. |
| 2005/0080460 A1 | 4/2005 | Wang et al. |
| 2005/0085743 A1 | 4/2005 | Hacker et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177061 A1 | 8/2005 | Alanen et al. |
| 2005/0177062 A1 | 8/2005 | Skrabal et al. |
| 2005/0192488 A1 | 9/2005 | Bryenton et al. |
| 2005/0201598 A1 | 9/2005 | Harel et al. |
| 2005/0203435 A1 | 9/2005 | Nakada |
| 2005/0203436 A1 | 9/2005 | Davies |
| 2005/0215918 A1 | 9/2005 | Frantz et al. |
| 2005/0228309 A1 | 10/2005 | Fisher et al. |
| 2005/0251062 A1 | 11/2005 | Choi et al. |
| 2005/0261743 A1 | 11/2005 | Kroll |
| 2005/0283091 A1 | 12/2005 | Kink et al. |
| 2006/0004300 A1 | 1/2006 | Kennedy |
| 2006/0025701 A1 | 2/2006 | Kasahara |
| 2006/0041280 A1 | 2/2006 | Stahmann et al. |
| 2006/0047189 A1* | 3/2006 | Takehara ............ 600/300 |
| 2006/0052678 A1 | 3/2006 | Drinan |
| 2006/0064029 A1 | 3/2006 | Arad |
| 2006/0070623 A1 | 4/2006 | Wilkinson et al. |
| 2006/0085048 A1 | 4/2006 | Cory et al. |
| 2006/0085049 A1 | 4/2006 | Cory et al. |
| 2006/0100532 A1 | 5/2006 | Bae et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0135886 A1 | 6/2006 | Lippert |
| 2006/0184060 A1 | 8/2006 | Belalcazar |
| 2006/0197509 A1 | 9/2006 | Kanamori et al. |
| 2006/0200033 A1 | 9/2006 | Keren et al. |
| 2006/0224079 A1* | 10/2006 | Washchuk ............ 600/547 |
| 2006/0224080 A1 | 10/2006 | Oku et al. |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0252670 A1 | 11/2006 | Fiorucci et al. |
| 2006/0253016 A1 | 11/2006 | Baker et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | Mcadams |
| 2007/0007975 A1 | 1/2007 | Hawkins et al. |
| 2007/0010758 A1 | 1/2007 | Matthiessen et al. |
| 2007/0024310 A1 | 2/2007 | Tokuno et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0088227 A1 | 4/2007 | Nishimura |
| 2007/0106342 A1 | 5/2007 | Schumann |
| 2007/0118027 A1 | 5/2007 | Baker et al. |
| 2007/0156061 A1 | 7/2007 | Hess |
| 2007/0188219 A1 | 8/2007 | Segarra |
| 2007/0246046 A1 | 10/2007 | Teschner et al. |
| 2007/0270707 A1 | 11/2007 | Belalcazar |
| 2008/0001608 A1 | 1/2008 | Saulnier |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0027350 A1 | 1/2008 | Webler et al. |
| 2008/0039700 A1 | 2/2008 | Drinan et al. |
| 2008/0048786 A1 | 2/2008 | Feldkamp et al. |
| 2008/0051643 A1 | 2/2008 | Park et al. |
| 2008/0064981 A1 | 3/2008 | Gregory |
| 2008/0091114 A1 | 4/2008 | Min et al. |
| 2008/0139957 A1 | 6/2008 | Hubbard et al. |
| 2008/0183098 A1 | 7/2008 | Denison et al. |
| 2008/0188757 A1 | 8/2008 | Rovira et al. |
| 2008/0200802 A1 | 8/2008 | Bhavaraju et al. |
| 2008/0205717 A1 | 8/2008 | Reeves et al. |
| 2008/0221411 A1 | 9/2008 | Hausmann et al. |
| 2008/0247502 A1 | 10/2008 | Liao |
| 2008/0252304 A1 | 10/2008 | Woo et al. |
| 2008/0262375 A1 | 10/2008 | Brown et al. |
| 2008/0270051 A1 | 10/2008 | Essex et al. |
| 2008/0287823 A1 | 11/2008 | Chetham |
| 2008/0306400 A1* | 12/2008 | Takehara ............ A61B 5/0537 600/547 |
| 2008/0306402 A1 | 12/2008 | Singer |
| 2008/0319336 A1 | 12/2008 | Ward et al. |
| 2009/0018432 A1 | 1/2009 | He |
| 2009/0043222 A1 | 2/2009 | Chetham |
| 2009/0054952 A1 | 2/2009 | Glukhovsky et al. |
| 2009/0069708 A1 | 3/2009 | Hatlestad et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0076410 A1 | 3/2009 | Libbus et al. |
| 2009/0082679 A1 | 3/2009 | Chetham |
| 2009/0084674 A1 | 4/2009 | Holzhacker et al. |
| 2009/0093730 A1 | 4/2009 | Grassl |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0209828 A1 | 8/2009 | Musin |
| 2009/0209872 A1 | 8/2009 | Pop |
| 2009/0216140 A1 | 8/2009 | Skrabal |
| 2009/0216148 A1 | 8/2009 | Freed et al. |
| 2009/0234244 A1 | 9/2009 | Tanaka |
| 2009/0240163 A1 | 9/2009 | Webler |
| 2009/0264727 A1 | 10/2009 | Markowitz |
| 2009/0264745 A1 | 10/2009 | Markowitz et al. |
| 2009/0264776 A1 | 10/2009 | Vardy |
| 2009/0264791 A1 | 10/2009 | Gregory et al. |
| 2009/0275854 A1 | 11/2009 | Zielinski et al. |
| 2009/0275855 A1 | 11/2009 | Zielinski et al. |
| 2009/0287102 A1 | 11/2009 | Ward |
| 2009/0306535 A1 | 12/2009 | Davies et al. |
| 2009/0318778 A1 | 12/2009 | Dacso et al. |
| 2009/0326408 A1 | 12/2009 | Moon |
| 2010/0007357 A1 | 1/2010 | Spielberger et al. |
| 2010/0049077 A1 | 2/2010 | Sadleir et al. |
| 2010/0056881 A1 | 3/2010 | Libbus et al. |
| 2010/0094160 A1 | 4/2010 | Eror et al. |
| 2010/0100003 A1 | 4/2010 | Chetham et al. |
| 2010/0100146 A1 | 4/2010 | Blomqvist |
| 2010/0106046 A1 | 4/2010 | Shochat et al. |
| 2010/0152605 A1 | 6/2010 | Ward |
| 2010/0168530 A1 | 7/2010 | Chetham et al. |
| 2010/0191141 A1 | 7/2010 | Aberg |
| 2010/0228143 A1 | 9/2010 | Teschner et al. |
| 2011/0025348 A1 | 2/2011 | Chetham et al. |
| 2011/0034806 A1 | 2/2011 | Hartov et al. |
| 2011/0046505 A1 | 2/2011 | Cornish et al. |
| 2011/0054343 A1 | 3/2011 | Chetham et al. |
| 2011/0054344 A1 | 3/2011 | Slizynski |
| 2011/0060239 A1 | 3/2011 | Gaw |
| 2011/0060241 A1 | 3/2011 | Martinsen et al. |
| 2011/0082383 A1 | 4/2011 | Cory et al. |
| 2011/0087129 A1 | 4/2011 | Chetham et al. |
| 2011/0118619 A1 | 5/2011 | Burton et al. |
| 2011/0190655 A1 | 8/2011 | Moissl et al. |
| 2011/0208084 A1 | 8/2011 | Martinez et al. |
| 2011/0230784 A2 | 9/2011 | Slizynski et al. |
| 2011/0245712 A1 | 10/2011 | Patterson et al. |
| 2011/0251513 A1 | 10/2011 | Chetham et al. |
| 2011/0274327 A1 | 11/2011 | Wehnes et al. |
| 2011/0282180 A1 | 11/2011 | Goldkuhl et al. |
| 2012/0071772 A1 | 3/2012 | Chetham |
| 2012/0165884 A1 | 6/2012 | Xi |
| 2012/0238896 A1 | 9/2012 | Garber et al. |
| 2013/0102873 A1 | 4/2013 | Hamaguchi |

(56) References Cited

U.S. PATENT DOCUMENTS

| | | | |
|---|---|---|---|
| 2013/0165760 A1 | 6/2013 | Erlinger et al. | |
| 2013/0165761 A1 | 6/2013 | De Limon et al. | |
| 2014/0148721 A1 | 5/2014 | Erlinger et al. | |
| 2014/0371566 A1 | 12/2014 | Raymond et al. | |

FOREIGN PATENT DOCUMENTS

| | | |
|---|---|---|
| CA | 2613524 | 1/2007 |
| CA | 2615845 | 1/2007 |
| CN | 1236597 | 12/1999 |
| CN | 1329875 | 1/2002 |
| EP | 0357309 | 3/1990 |
| EP | 377887 | 7/1990 |
| EP | 581073 | 2/1994 |
| EP | 339471 | 3/1997 |
| EP | 865763 | 9/1998 |
| EP | 0869360 | 10/1998 |
| EP | 1078597 | 2/2001 |
| EP | 1080686 | 3/2001 |
| EP | 1112715 | 4/2001 |
| EP | 1112715 | 7/2001 |
| EP | 1146344 | 10/2001 |
| EP | 1114610 | 11/2001 |
| EP | 1177760 | 2/2002 |
| EP | 1219937 | 7/2002 |
| EP | 1238630 | 9/2002 |
| EP | 1247487 | 10/2002 |
| EP | 1329190 | 7/2003 |
| EP | 1338246 | 8/2003 |
| EP | 1080686 | 3/2004 |
| EP | 1452131 | 9/2004 |
| EP | 1553871 | 7/2005 |
| EP | 1118308 | 11/2005 |
| EP | 1629772 | 3/2006 |
| EP | 1247487 | 1/2008 |
| EP | 1903938 | 4/2008 |
| EP | 1909642 | 4/2008 |
| EP | 1948017 | 7/2008 |
| EP | 1353595 | 8/2008 |
| FR | 2748928 | 11/1997 |
| GB | 1441622 | 7/1976 |
| GB | 2131558 | 6/1984 |
| GB | 2260416 | 4/1993 |
| GB | 2426824 | 12/2006 |
| JP | 6-74103 | 10/1994 |
| JP | 8191808 | 7/1996 |
| JP | 10225521 | 8/1998 |
| JP | 2000107138 | 4/2000 |
| JP | 2001037735 | 2/2001 |
| JP | 2001061804 | 3/2001 |
| JP | 2001-204707 | 7/2001 |
| JP | 2001224568 | 8/2001 |
| JP | 2001-245866 | 9/2001 |
| JP | 2002502274 | 1/2002 |
| JP | 2002238870 | 8/2002 |
| JP | 2002350477 | 12/2002 |
| JP | 2003-502092 | 1/2003 |
| JP | 2003075487 | 3/2003 |
| JP | 2003-116803 | 4/2003 |
| JP | 2003116805 | 4/2003 |
| JP | 2003230547 | 8/2003 |
| JP | 200461251 | 2/2004 |
| JP | 2006-501892 | 1/2006 |
| JP | 2008-502382 | 1/2008 |
| JP | 2010-526604 | 8/2010 |
| RU | 2112416 | 6/1998 |
| WO | WO 88-07392 | 10/1988 |
| WO | WO 91-19454 | 12/1991 |
| WO | WO 93-18821 | 9/1993 |
| WO | WO 94/01040 | 1/1994 |
| WO | WO 94-10922 | 5/1994 |
| WO | WO 96-01586 | 1/1996 |
| WO | WO 96-12439 | 5/1996 |
| WO | WO 96-32652 | 10/1996 |
| WO | WO 97-11638 | 4/1997 |
| WO | WO 97-14358 | 4/1997 |
| WO | WO 97-24156 | 7/1997 |
| WO | WO 98-06328 | 2/1998 |
| WO | WO 98/12983 | 4/1998 |
| WO | WO 98-23204 | 6/1998 |
| WO | WO 98-33553 | 8/1998 |
| WO | WO 98-51211 | 11/1998 |
| WO | WO 99-42034 | 8/1999 |
| WO | WO 99-48422 | 9/1999 |
| WO | WO 00-19886 | 4/2000 |
| WO | WO 00-40955 | 7/2000 |
| WO | WO 00-78213 | 12/2000 |
| WO | WO 00-79255 | 12/2000 |
| WO | WO 01-27605 | 4/2001 |
| WO | WO 01-50954 | 7/2001 |
| WO | WO 01-52733 | 7/2001 |
| WO | WO 01/67098 A1 * | 9/2001 |
| WO | WO 02-053028 | 7/2002 |
| WO | WO 02-062214 | 8/2002 |
| WO | WO 02-094096 | 11/2002 |
| WO | WO 2004-000115 | 12/2003 |
| WO | WO 2004/002301 | 1/2004 |
| WO | WO 2004/006660 | 1/2004 |
| WO | WO 2004-021880 | 3/2004 |
| WO | WO 2004-026136 | 4/2004 |
| WO | WO 2004-030535 | 4/2004 |
| WO | WO 2004-032738 | 4/2004 |
| WO | WO 2004-043252 | 5/2004 |
| WO | WO 2004-047635 | 6/2004 |
| WO | WO 2004-047636 | 6/2004 |
| WO | WO 2004-047638 | 6/2004 |
| WO | WO 2004-049936 | 6/2004 |
| WO | WO 2004-083804 | 9/2004 |
| WO | WO 2004-084087 | 9/2004 |
| WO | WO 2004-084723 | 10/2004 |
| WO | WO 2004-098389 | 11/2004 |
| WO | WO 2004/112563 | 12/2004 |
| WO | WO 2005-010640 | 2/2005 |
| WO | WO 2005-018432 | 3/2005 |
| WO | WO 2005-027717 | 3/2005 |
| WO | WO 2005-051163 | 6/2005 |
| WO | WO 2005-051194 | 6/2005 |
| WO | WO 2005-122881 | 12/2005 |
| WO | WO 2005-122888 | 12/2005 |
| WO | WO 2006-045051 | 4/2006 |
| WO | WO 2006-056074 | 6/2006 |
| WO | WO 2006-129108 | 12/2006 |
| WO | WO 2006-129116 | 12/2006 |
| WO | WO 2007-002991 | 1/2007 |
| WO | WO 2007-002992 | 1/2007 |
| WO | WO 2007-002993 | 1/2007 |
| WO | WO 2007-009183 | 1/2007 |
| WO | WO 2007/045006 | 4/2007 |
| WO | WO 2007041783 A1 * | 4/2007 |
| WO | WO 2007-056493 | 5/2007 |
| WO | WO 2007-070997 | 6/2007 |
| WO | WO 2007/105996 | 9/2007 |
| WO | WO 2007-128952 | 11/2007 |
| WO | WO 2008-011716 | 1/2008 |
| WO | WO 2008-054426 | 8/2008 |
| WO | WO 2008/119166 | 10/2008 |
| WO | WO 2008-119166 | 10/2008 |
| WO | WO 2008-138062 | 11/2008 |
| WO | WO 2008/149125 | 12/2008 |
| WO | WO 2009-018620 | 2/2009 |
| WO | WO 2009-027812 | 3/2009 |
| WO | WO 2009-036369 | 3/2009 |
| WO | WO 2009-068961 | 6/2009 |
| WO | WO 2009/100491 | 8/2009 |
| WO | WO 2009-112965 | 9/2009 |
| WO | WO 2010-003162 | 1/2010 |
| WO | WO 2010-029465 | 3/2010 |
| WO | WO 2010-069023 | 6/2010 |
| WO | WO 2010-076719 | 7/2010 |
| WO | WO 2011-018744 | 2/2011 |
| WO | WO 2011-022068 | 2/2011 |
| WO | WO 2011-050393 | 5/2011 |
| WO | WO 2011-075769 | 6/2011 |

(56) References Cited

FOREIGN PATENT DOCUMENTS

| WO | WO 2011-113169 | 9/2011 |
|---|---|---|
| WO | WO 2011-136867 | 11/2011 |
| WO | WO 2014-176420 | 10/2014 |

OTHER PUBLICATIONS

Locus, www.dictionary.com, printed Nov. 21, 2016 (6 pages).*
Cornish, et al., "Optimizing Electrode Sites for Segmental Bioimpedance Measurements" Physiological Measurement, Institute of Physics, 1999, pp. 241-250, vol. 20, No. 3.
Cornish, et al., "A New Technique for the Quantification of Peripheral Edema with Application in Both Unilateral and Bilateral Cases" Angiology, 2002, pp. 41-47, vol. 53, No. 1.
Fenech, et al., "Extracellular and Intracellular Volume Variations During Postural Change Measured by Segmental and Wrist-Ankle Bioimpedance Spectroscopy" IEEE Transactions on Biomedical Engineering, IEEE Service Center, 2004, pp. 166-175, vol. 51, No. 1.
Golden, et al., "Assessment of Peripheral Hemodynmics using Impedance Plethysmogrphy" Physical Therapy, 1986, pp. 1544-1547, vol. 66, No. 10.
Kim, et al., "Impedance Tomography and its Application in Deep Venous Thrombosis Detection" IEEE Engineering in Medicine and Biology Magazine, IEEE Service Center, 1989, pp. 46-49, vol. 8, No. 1.
Nawarycz, et al., "triple-frequency Electroimpedance Method for Evaluation of Body Water Compartments" Medical & Biological Engineering & Computing, 1996, pp. 181-182, vol. 34, No. Supp. 01, Pt. 02.
Noshiro, et al., "Electrical Impedance in the Lower Limbs of Patients with Duchenne Muscular Dystrophy: A Preliminary Study" Medical & Biological Engineering & Computing, 1993, pp. 97-102, vol. 31, No. 2.
Seo, et al., "Measuring Lower Leg Swelling: Optimum Frequency for Impedance Method" Medical &, Biological Engineering & Computing, 2001, pp. 185-189, vol. 39.
Seoane, et al., "Current Source for Wideband Electrical Bioimpedance Spectroscopy Based on a Single Operational Amplifier" World Congress on Medical Physics and Biomedical Engineering 2006, pp. 707-710, vol. 14.
Smith, et al., "A Pilot Study for Tissue Characterization Using Bio-impedance Mapping" 13th International Conference on Electrical Bio-impedance and the 8th Conference on Electrical Impedance Tomography 2007, pp. 146-149.
Stanton, et al., "Non-invasive Assessment of the Lymphedematous Limb" The International Society of Lymphology, 2000, pp. 122-135, vol. 33, No. 3.
Abdullah M. Z.; Simulation of an inverse problem in electrical impedance tomography using resistance electrical network analogues; International Journal of Electrical Engineering Education; vol. 36, No. 4, pp. 311-324; Oct. 1999.
Al-Hatib, F.; Patient Instrument connection errors in bioelectrical impedance measurement; Physiological Measurement; vol. 19, No. 2, pp. 285-296; May 2, 1998.
Bella, et al., Relations of Left Ventricular Mass to Fat-Free and Adipose Body Mass: The Strong Heart Study, (1998) Circulation, vol. 98, pp. 2538-2544.
Boulier, A. et al.; Fat-Free Mass Estimation by Two Electrode Impedance Method; American Journal of Clinical Nutrition; vol. 52, pp. 581-585; 1990.
Bracco, D. et al., Bedside determination of fluid accumulation after cardiac surgery using segmental bioelectrical impedance, Critical Care Medicine, vol. 26, No. 6, pp. 1065-1070, 1998.
Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.
Cornish, B.H. et al.; Alteration of the extracellular and total body water volumes measured by multiple frequency bioelectrical impedance analysis; Nutrition Research; vol. 14, No. 5, pp. 717-727; 1994.
Cornish, B.H. et al.; Bioelectrical impedance for monitoring the efficacy of lymphoedema treatment programmes; Breast Cancer Research and Treatment; vol. 38, pp. 169-176; 1996.
Cornish, B.H. et al.; Data analysis in multiple-frequency bioelectrical impedance analysis; Physiological Measurement; vol. 19, No. 2, pp. 275-283; May 1, 1998.
Cornish, B.H. et al.; Early diagnosis of lymphedema using multiple frequency bioimpedance; Lymphology; vol. 34, pp. 2-11; Mar. 2001.
Cornish, B.H. et al.; Early diagnosis of lymphoedema in postsurgery breast cancer patients; Annals New York Academy of Sciences; pp. 571-575; May 2000.
Cornish, B.H. et al.; Quantification of Lymphoedema using Multi-frequency Bioimpedance; Applied Radiation and Isotopes; vol. 49, No. 5/6, pp. 651-652; 1998.
De Luca, F. et al., Use of low-frequency electrical impedance measurements to determine phospoholipid content in amniotic fluid; Physics in Medicine and Biology, vol. 41, pp. 1863-1869, 1996.
Deurenberg, P. et al., Multi-frequency bioelectrical impedance: a comparison between the Cole-Cole modelling and Hanai equations with the classically impedance index approach, Annals of Human Biology, vol. 23, No. 1, pp. 31-40, 1996.
Dines K.A. et al.; Analysis of electrical conductivity imaging; Geophysics; vol. 46, No. 7, pp. 1025-1036; Jul. 1981.
Ellis, K.J. et al; Human hydrometry: comparison of multifrequency bioelectrical impedance with 2H2O and bromine dilution; Journal of Applied Physiology; vol. 85, No. 3, pp. 1056-1062; 1998.
Ezenwa, B.N. et al.; Multiple Frequency System for Body Composition Measurement; Proceedings of the Annual International Conference of the Engineering in Medicine and Biology Society; vol. 15; pp. 1020-1021; 1993.
Forslund, A.H. et al.; Evaluation of modified multicompartment models to calculate body composition in healthy males; American Journal of Clinical Nutrition; vol. 63, pp. 856-862; 1996.
Gersing, E.; Impedance spectroscopy on living tissue for determination of the state of Organs; Bioelectrochemistry and Bioenergetics; vol. 45, pp. 145-149; 1998.
Gerth, W.A. et al.; A computer-based bioelectrical impedance spectroscopic system for noninvasive assessment of compartmental fluid redistribution; Third Annual IEEE Symposium on Computer Based Medical Systems, Jun. 3-6, 1990, University of NC. At Chapel Hill; pp. 446-453; Jun. 1990.
Gudivaka R. et al; Single- and multifrequency models for bioelectrical impedance analysis of body water compartments; Applied Physiology; vol. 87, Issue 3, pp. 1087-1096; 1999.
Iacobellis, G., et al. Influence of Excess Fat on Cardiac Morphology and Function: Study in Uncomplicated Obesity, (2002) Obesity Research, vol. 10, pp. 767-773.
Jones, C.H. et al; Extracellular fluid volume determined by bioelectric impedance and serum albumin in CAPD patients; Nephrology Dialysis Transplantation; vol. 13, pp. 393-397; 1998.
Jossinet, J. et al.; A Study for Breast Imaging with a Circular Array of Impedance Electrodes; Proc. Vth Int. Conf. Bioelectrical Impedance, 1981, Tokyo, Japan; pp. 83-86; 1981.
Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1.p. 289; 1988.
Kanai, H. et al.; Electrical Measurement of Fluid Distribution in Legs and Arms; Medical Progress through technology; pp. 159-170; 1987.
Karason, K., et al., Impact of Blood Pressure and Insulin on the Relationship Between Body Fat and Left Ventricular Structure, (2003) European Heart Journal, vol. 24, pp. 1500-1505.
Liu R. et al; Primary Multi-frequency Data Analyze in Electrical Impedance Scanning; Proceedings of the IEEE-EMBS 2005, 27th Annual International Conference of the Engineering in Medicine and Biology Society, Shanghai, China; pp. 1504-1507; , Sep. 1-4, 2005.

(56) References Cited

OTHER PUBLICATIONS

Lozano, A. et al.; Two-frequency impedance plethysmograph: real and imaginary parts; Medical & Biological Engineering & Computing; vol. 28, No. 1, pp. 38-42; Jan. 1990.

Lukaski, H.C. et al.; Estimation of Body Fluid Volumes Using Tetrapolar Bioelectrical Impedance Measurements; Aviation, Space, and Environmental Medicine; pp. 1163-1169; Dec. 1988.

Man, B. et al. Results of Preclinical Tests for Breast Cancer Detection by Dielectric Measurements; XII Int. Conf. Med. Biol. Engng. 1979, Jerusalem, Israel. Springer Int., Berlin; Section 30.4; 1980.

Mattar, J.A., Application of Total Body Impedance to the Critically Ill Patient, New Horizons, vol. 4, No. 4, pp. 493-503, Nov. 1996.

McCullah, et al.; Bioelectrical Impedance Analysis Measures the Ejection Fraction of the Calf Muscle Pump; IFMBE Proceedings; vol. 17, pp. 616-619; 2007.

McDougal D., et al.; Body Composition Measurements From Whole Body Resistance and Reactance; Surgical Forum; vol. 36, pp. 43-44; 1986.

Osterman K.S. et al.; Multifrequency electrical impedance imaging: preliminary in vivo experience in breast; Physiological Measurement; vol. 21, No. 1, pp. 99-109; Feb. 2000.

Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.

Pethig, R. et al.; The Passive Electrical Properties of Biological Systems: Their Significance in Physiology, Biophysics and Biotechnology; Physics in Medicine and Biology; vol. 32, pp. 933-970; 1987.

Piperno, G. et al.; Breast Cancer Screening by Impedance Measurements; Frontiers of Medical & Biological Engineering; vol. 2, pp. 111-117; 1990.

Rigaud, B. et al.; Bioelectrical Impedance Techniques in Medicine; Critical Reviews in Biomedical Engineering; vol. 24 (4-6), pp. 257-351; 1996.

Scharfetter, H. et al.; Effect of Postural Changes on the Reliability of Volume Estimations from Bioimpedance Spectroscopy Data; Kidney International; vol. 51, No. 4, pp. 1078-2087; 1997.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.

Skidmore, R. et al.; A Data Collection System for Gathering Electrical Impedance Measurements from the Human Breast; Clinical Physics Physiological Measurement; vol. 8, pp. 99-102; 1987.

Sollish, B.D. et al.; Microprocessor-assisted Screening Techniques; Israel Journal of Medical Sciences; vol. 17, pp. 859-864; 1981.

Steijaert, M. et al.; The use of multi-frequency impedance to determine total body water and extracellular water in obese and lean female individuals; International Journal of Obesity; vol. 21, pp. 930-934; 1997.

Surowiec, A.J. et al.; Dielectric Properties of Brest Carcinoma and the Surrounding Tissues; IEEE Transactions on Biomedical Engineering; vol. 35, pp. 257-263; 1988.

Tedner, B.; Equipment Using Impedance Technique for Automatic Recording of Fluid-Volume Changes During Haemodialysis; Medical & Biological Engineering & Computing; pp. 285-290; 1983.

Thomas. B.J. et al.; Bioelectrical impedance analysis for measurement of body fluid volumes—A review; Journal of Clinical Engineering; vol. 17, No. 16, pp. 505-510; 1992.

Thomas. B.J. et al.; Bioimpedance Spectrometry in Determination of Body Water Compartments: Accuracy and Clinical Significance; Applied Radiation and Isotopes; vol. 49, No. 5/6, pp. 447-455; 1998.

Thomas. B.J.; Future Technologies; Asia Pacific Journal Clinical Nutrition; vol. 4, pp. 157-159; 1995.

Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.

Ward, L.C. et al., Multi-frequency bioelectrical impedance augments the diagnosis and management of lymphoedema in postmastectomy patients, European Journal of Clinical Investigation, vol. 22, pp. 751-754, 1992.

Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.

Ward, L.C. et al.; There is a better way to measure Lymphoedema; National Lymphedema Network Newsletter; vol. 7, No. 4, pp. 89-92; Oct. 1995.

Woodrow, G. et al; Effects of icodextrin in automated peritoneal dialysis on blood pressure and bioelectrical impedance analysis; Nephrology Dialysis Transplantation; vol. 15, pp. 862-866; 2000.

Yamakoshi, K.; Non-Invasive Cardiovascular Hemodynamic Measurements; Sensors in Medicine and Health Care; pp. 107-160; 2004.

Yoshinaga, M., Effect of Total Adipose Weight and Systemic Hypertension on Left Ventricular Mass in Children, American Journal of Cardiology, (1995) vol. 76, pp. 785-787.

Blad et al.; Impedance Spectra of Tumour Tissue in Tomparison with Normal Tissue; A Possible Clinical Application for Electrical Impedance Tomography; Physiological Measurement; vol. 17, pp. A105-A115; 1996.

De Lorenzo et al.; Determination of Intracellular Water by Multifrequency Bioelectrical Impedance; Ann. Nutr. Metab.; vol. 39, pp. 177-184; 1995.

Edwards, L.S.; A Modified Pseudosection for Resistivity and IP; Geophysics; vol. 42, No. 5, pp. 1020-1036; 1977.

Hansen, E.; On the Influence of Shape and Variations in Conductivity of the Sample on Four-Point Measurements; Applied Scientific Research; Section B; vol. 8, Issue 1, pp. 93-104 1960.

Igel, J.; On the Small-Scale Variability of Electrical Soil Properties and Its Influence on Geophysical Measurements; Ph.D. Thesis; Frankfurt University; Hanover, Germany; p. 188; 2007.

Kyle et al.; Bioelectrical Impedance Analysis—Part I: Review of Principles and Methods; Clinical Nutrition; vol. 23, pp. 1226-1243; 2004.

Loke et al.; Least Squares Deconvolution of Apparent Resistivity Pseudosections; Geophysics; vol. 60, No. 6, pp. 1682-1690; 1995.

McAdams et al; Tissue Impedance: a Historical Overview Physiological Measurement; Institute of Physics Publishing; vol. 16. (3A), pp. A1-A13; 1995.

McEwan et al.; Battery Powered and Wireless Electrical Impedance Tomography Spectroscopy Imaging Ssing Bluetooth; Medicon IFMBE Proceedings; vol. 16, pp. 798-801; 2007.

Roy, A.; Depth of investigation in Direct Current Methods Geophysics; vol. 36, pp. 943-959; 1971.

Wilson et al.; Feasibility Studies of Electrical Impedance Spectroscopy for Monitoring Tissue Response to Photodynamic Therapy; Optical Methods for Tumor Treatment and Detections: Mechanisms and Techniques in Photodynamic Therapy VII; Proc. SPIE 3247; pp. 69-80; 1998.

International Search Report and Written Opinion of the International Searching Authority issued in PCT/AU2009/000163 dated Apr. 16, 2009.

International Search Report and Written Opinion of the International Searching Authority issued in PCT/AU2006/000922 dated Oct. 13, 2006.

International Search Report and Written Opinion of the International Searching Authority issued in PCT/AU2006/001057 dated Oct. 25, 2006.

International Search Report and Written Opinion of the International Searching Authority issued in PCT/AU2008/000034 dated Mar. 17, 2008.

International Search Report and Written Opinion of the International Searching Authority issued in PCT/CA2008/000588 dated Aug. 13, 2008.

(56) References Cited

OTHER PUBLICATIONS

International Search Report and Written Opinion of the International Searching Authority issued in PCT/AU2006/000924 dated Oct. 5, 2006.

International Search Report and Written Opinion of the International Searching Authority issued in PCT/AU2008/001521 dated Jan. 15, 2009.

* cited by examiner

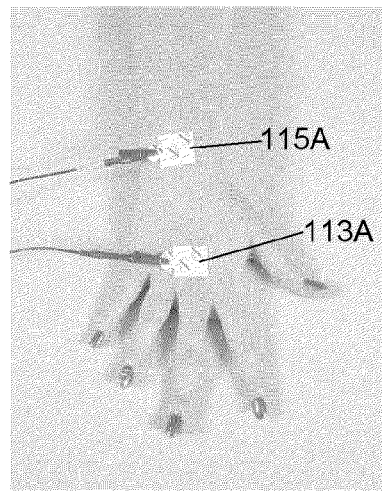 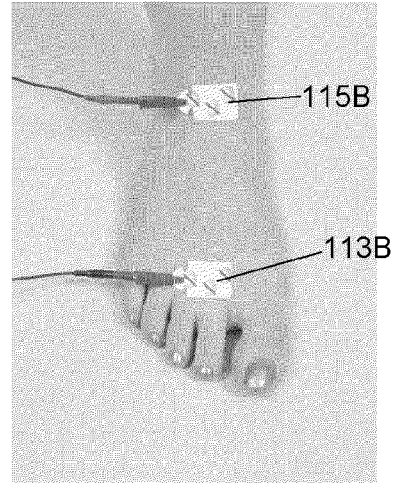
Fig. 5A  Fig. 5B
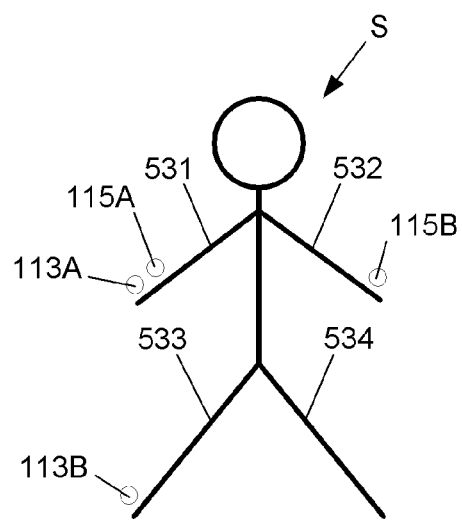 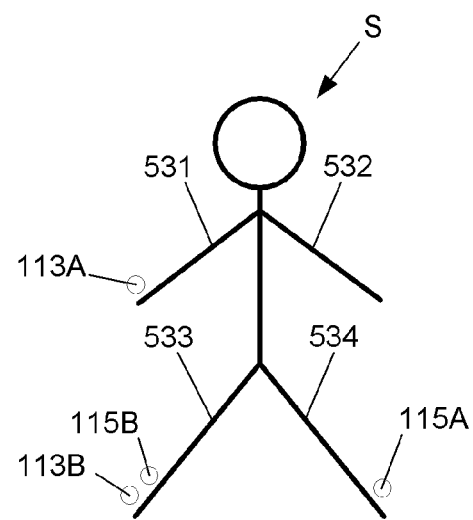
Fig. 5C  Fig. 5D

FLUID LEVEL INDICATOR DETERMINATION

RELATED APPLICATIONS

This application is a U.S. National Phase under 35 U.S.C. §371 of the International Patent Application No. PCT/AU2010/001399, filed Oct. 21, 2010, and published in English on May 5, 2011 as WO 2011/050393, which claims the benefit of Australian Patent Application No. 2009905220, filed Oct. 26, 2009, both of which are incorporated by reference in their entirety.

BACKGROUND OF THE INVENTION

The present invention relates to a method and apparatus for use in analysing impedance measurements performed on a subject, and in particular to a method and apparatus for determining an indicator using a dispersion parameter, to thereby allow the indicator to be used in diagnosing the presence, absence or degree of oedema.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological parameters relating to a subject, such as fluid levels, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema, or other conditions which affect body habitus.

Lymphoedema is a condition characterised by excess protein and oedema in the tissues as a result of reduced lymphatic transport capacity and/or reduced tissue proteolytic capacity in the presence of a normal lymphatic load. Acquired, or secondary lymphoedema, is caused by damaged or blocked lymphatic vessels. The commonest inciting events are surgery and/or radiotherapy. However, onset of lymphoedema is unpredictable and may develop within days of its cause or at any time during a period of many years after that cause.

WO00/79255 describes a method of detection of oedema by measuring bioelectrical impedance at two different anatomical regions in the same subject at a single low frequency alternating current. The two measurements are analysed to obtain an indication of the presence of tissue oedema by comparing with data obtained from a normal population.

WO2005/122888 describes a method of detecting tissue oedema in a subject. The method includes determining a measured impedance for first and second body segments. An index indicative of a ratio of the extra-cellular to intra-cellular fluid is then calculated for each body segment, with these being used to determine an index ratio, based on the index for the first and second body segments. The index ratio can in turn be used to determine the presence, absence or degree of tissue oedema, for example by comparing the index ratio to a reference or previously determined index ratios.

WO2008/138602 describes a method for use in analysing impedance measurements performed on a subject, the method including, in a processing system determining at least one impedance value, representing the impedance of at least a segment of the subject, determining an indicator indicative of a subject parameter using the at least one impedance value and a reference and displaying a representation of the indicator.

SUMMARY OF THE PRESENT INVENTION

It is an object of the present invention to substantially overcome, or at least ameliorate, one or more disadvantages of existing arrangements.

In a first broad form the present invention seeks to provide a method for use in analysing impedance measurements performed on a subject, the method including, in a processing system:
   a) determining at least one impedance value at each of a number of frequencies, each impedance value representing the impedance of a segment of the subject;
   b) determining a dispersion parameter value indicative of a dispersion of the impedance values; and,
   c) determining an indicator based at least in part on the dispersion parameter value.

Typically the method includes, in the processing system:
   a) determining first and second dispersion parameter values for first and second body segments respectively; and,
   b) determining the indicator using the first and second dispersion parameter values.

Typically the first body segment is an affected body segment and the second body segment is an unaffected body segment.

Typically at least one of the body segments is a dominant limb and the other body segment is a non-dominant limb.

Typically the first body segment is a different body segment to the second body segment.

Typically the method includes, in the processing system:
   a) determining a predicted dispersion parameter value for the first body segment using the second dispersion parameter value;
   b) determining the indicator using the first and predicted dispersion parameter values.

Typically predicted dispersion parameter value is determined to take into account at least one of:
   a) limb dominance; and,
   b) differences in limb types.

Typically the method includes, in the processing system, determining a predicted dispersion parameter value using at least one reference value derived from a reference normal population.

Typically the reference normal population is selected based on at least one of:
   a) limb dominance;
   b) differences in limb types;
   c) ethnicity;
   d) age;
   e) gender;
   f) weight; and,
   g) height.

Typically the at least one reference value is determined based on a linear regression of first and second dispersion parameter values measured for the reference normal population.

Typically the method includes, in the processing system, determining the predicted dispersion parameter value using an equation of the form:

$$DP_p = aDP_2 + K$$

where:
- $DP_2$ is the second dispersion parameter value
- $DP_p$ is the predicted dispersion parameter value
- a is a multiplier reference value determined based on a relationship between first and second dispersion parameter values in a reference population
- K is a constant reference value determined based on a relationship between first and second dispersion parameter values in a reference population Typically, for a male subject, the predicted value for a leg segment based on second dispersion parameters for an arm segment is based on:
 a) a value of a in the range 0.15 to 0.022; and,
 b) a value of K in the range 0.62 to 0.72.

Typically, for a female subject, the predicted value for a leg segment based on second dispersion parameters for an arm segment is based on:
 a) a value of a in the range 0.44 to 0.41; and,
 b) a value of K in the range 0.43 to 0.46.

Typically the method includes, in the processing system, determining the indicator using the equation:

$$Ind = \frac{sf \times (DP_p - DP_1)}{3SE}$$

where:
- Ind is the indicator
- $DP_1$ is a dispersion parameter value determined for the body segment
- $DP_p$ is a predicted dispersion parameter value for the body segment
- sf is a scaling factor
- SE is a standard error determined based on dispersion parameter values in a reference population Typically the method includes, in the processing system, determining the indicator using the equation:

$$Ind = \frac{sf \times (DP_\mu - DP_1)}{3SE}$$

where:
- $DP_\mu$ is the mean dispersion parameter value for a reference normal population
- $DP_1$ is a dispersion parameter value determined for the body segment
- sf is a scaling factor
- SE is a standard error determined for the dispersion parameter values for the reference population Typically the scaling factor is selected so that a threshold value indicative of the presence or absence of oedema is an integer value.

Typically the method includes, in the processing system, determining the indicator based on the equation:

$$Ind = sf(DP_2 - DP_1)$$

where:
- Ind is the indicator
- $DP_1$ is a first dispersion parameter value for a first body segment
- $DP_2$ is a second dispersion parameter value for a second body segment
- sf is a scaling factor Typically the dispersion parameter value is indicative of the distribution of impedance measurements for the respective body segment.

Typically the dispersion parameter is based on the value of at least one of:

$$DP = \frac{(R_0 - R_\infty)}{X_c}$$

$$DP = \frac{X_c}{(R_0 - R_\infty)}$$

$$DP = \frac{(R_\infty - R_0)}{X_c}$$

$$DP = \frac{X_c}{(R_\infty - R_0)}$$

where:
- $R_\infty$ = impedance at infinite applied frequency;
- $R_0$ = impedance at zero applied frequency;
- $X_c$ = reactance at the centre of the circle.

Typically the dispersion parameter is based on the value of:

$$\alpha = \frac{2}{\pi} a\tan \frac{(R_0 - R_\infty)}{2|X_c|}$$

Typically the indicator is at least one of:
 a) an oedema indicator for use in assessing a presence, absence or degree of oedema in the subject.
 b) a hydration indicator for use in assessing hydration levels in a subject.

Typically the method includes, in the processing system, displaying a representation of the indicator.

Typically representation of the indicator includes a linear scale including:
 a) a linear indicator;
 b) a scale; and,
 c) a pointer, the pointer being positioned on the scale in accordance with the indicator.

Typically the method includes, in the processing system, displaying a representation including an indication of a change in indicator value from at least one of a previous indicator value and a baseline indicator value.

Typically the method includes, in the processing system:
 a) determining at least one threshold using a reference; and,
 b) displaying the threshold as part of the representation.

Typically the method includes, in the processing system:
 a) determining two thresholds using a reference; and,
 b) displaying the thresholds on the representation, the thresholds being indicative of a normal range.

Typically the method includes, in the processing system, displaying, on the representation, at least one of:
 a) a normal range;
 b) an intervention range;
 c) a hydration range; and,
 d) an oedema range.

Typically the method includes in the processing system, causing one or more impedance measurements to be performed.

Typically the method includes, in the processing system:
a) causing at least one excitation signal to be applied to the subject;
b) determining at least one signal measured across the subject; and,
c) determining at least one impedance value using an indication of the excitation signal and the signal measured across the subject.

Typically the method includes, in the processing system:
a) controlling a signal generator to thereby cause the at least one excitation signals to be applied to the subject; and,
b) determining the at least one signal measured across the subject using a sensor.

In a second broad form the present invention seeks to provide apparatus for use in analysing impedance measurements performed on a subject, the apparatus including a processing system for:
a) determining at least one impedance value at each of a number of frequencies, each impedance value representing the impedance of a segment of the subject;
b) determining a dispersion parameter value indicative of a dispersion of the impedance values; and,
c) determining an indicator based at least in part on the dispersion parameter value.

Typically the apparatus includes:
a) a signal generator for applying one or more electrical signals to the subject using a first set of electrodes;
b) a sensor for measuring electrical signals across a second set of electrodes applied to the subject; and,
c) a controller for:
 i) controlling the signal generator; and,
 ii) determining the indication of the measured electrical signals.

Typically the controller includes the processing system.
Typically the processing system includes the controller.

In a third broad form the present invention seeks to provide a method for use diagnosing the presence, absence or degree of oedema in a subject by using impedance measurements performed on the subject, the method including, in a processing system:
a) determining at least one impedance value at each of a number of frequencies, each impedance value representing the impedance of a segment of the subject;
b) determining a dispersion parameter value indicative of a dispersion of the impedance values;
c) determining an indicator based at least in part on the dispersion parameter value; and,
d) displaying a representation of the indicator, to thereby allow the presence, absence or degree of oedema in the subject to be assessed.

It will be appreciated that the broad forms of the invention may be used individually or in combination, and may be used for diagnosis of the presence, absence or degree of a range of conditions and illnesses, including, but not limited to oedema, lymphoedema, body composition and the like.

BRIEF DESCRIPTION OF THE DRAWINGS

An example of the present invention will now be described with reference to the accompanying drawings, in which:—

FIGS. 5A and 5B are diagrams of examples of electrode positions for use in measuring limb impedances;
FIGS. 5C and 5D are schematic diagrams of examples of electrode positions for use in measuring limb impedances.

DETAILED DESCRIPTION OF THE PREFERRED EMBODIMENTS

Figure 1:
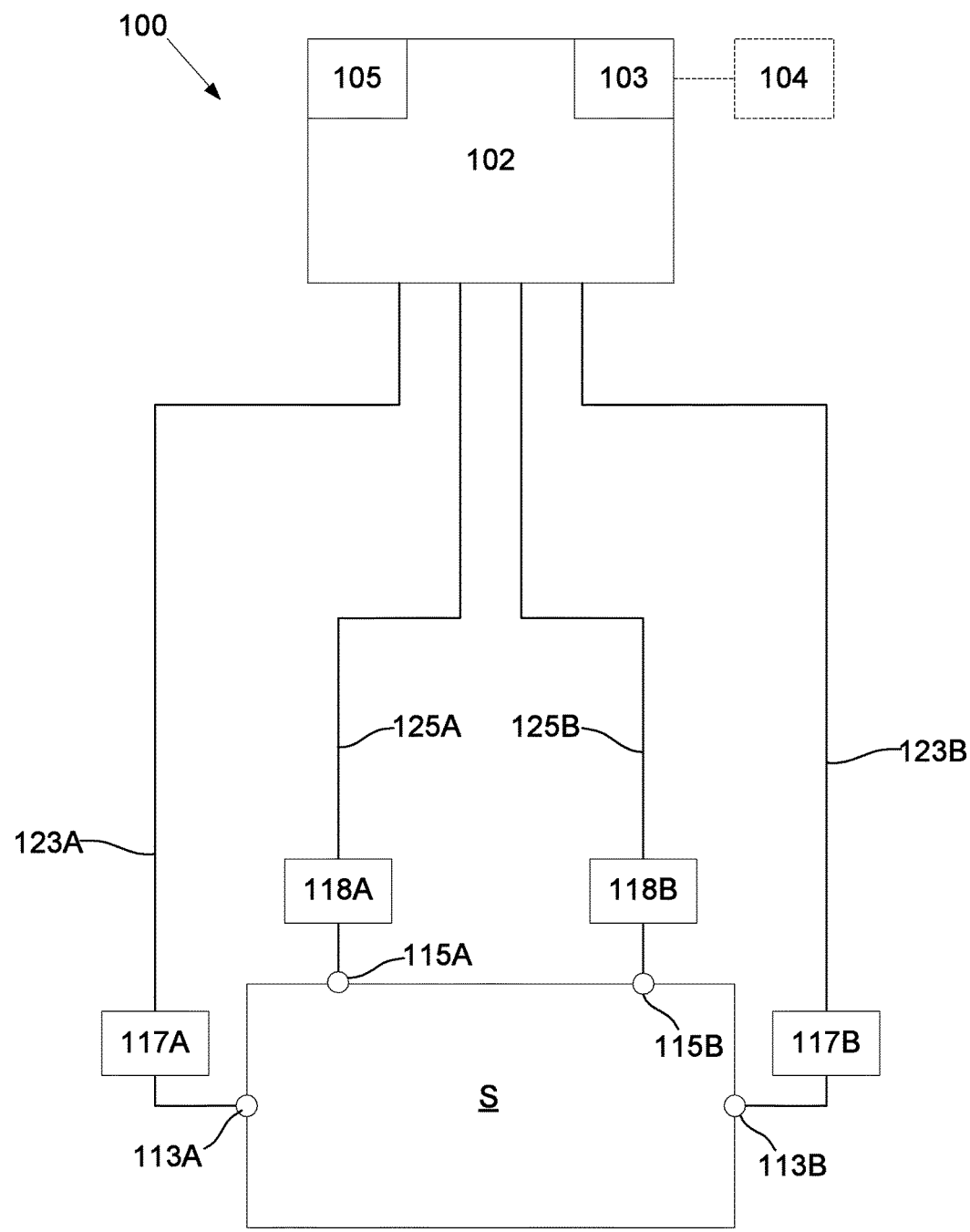
FIG. 1 is a schematic of an example of impedance determination apparatus.

An example of apparatus suitable for performing an analysis of a subject's bioelectric impedance will now be described with reference to FIG. 1.

As shown the apparatus includes a measuring device 100 including a processing system 102, connected to one or more signal generators 117A, 117B, via respective first leads 123A, 123B, and to one or more sensors 118A, 118B, via respective second leads 125A, 125B. The connection may be via a switching device, such as a multiplexer, although this is not essential.

In use, the signal generators 117A, 117B are coupled to two first electrodes 113A, 113B, which therefore act as drive electrodes to allow signals to be applied to the subject S, whilst the one or more sensors 118A, 118B are coupled to the second electrodes 115A, 115B, which act as sense electrodes, allowing signals across the subject S to be sensed.

The signal generators 117A, 117B and the sensors 118A, 118B may be provided at any position between the processing system 102 and the electrodes 113A, 113B, 115A, 115B, and may be integrated into the measuring device 100. However, in one example, the signal generators 117A, 117B and the sensors 118A, 118B are integrated into an electrode system, or another unit provided near the subject S, with the leads 123A, 123B, 125A, 125B connecting the signal generators 117A, 117B and the sensors 118A, 118B to the processing system 102.

It will be appreciated that the above described system is a two channel device, used to perform a classical four-terminal impedance measurement, with each channel being designated by the suffixes A, B respectively. The use of a two channel device is for the purpose of example only, and multiple channel devices can alternatively be used to allow multiple body segments to be measured without requiring reattachment of electrodes. An example of such a device is described in copending patent application number WO2009059351.

An optional external interface 103 can be used to couple the measuring device 100, via wired, wireless or network connections, to one or more peripheral devices 104, such as an external database or computer system, barcode scanner, or the like. The processing system 102 will also typically include an I/O device 105, which may be of any suitable form such as a touch screen, a keypad and display, or the like.

In use, the processing system 102 is adapted to generate control signals, which cause the signal generators 117A, 117B to generate one or more alternating signals, such as voltage or current signals of an appropriate waveform, which can be applied to a subject S, via the first electrodes 113A, 113B. The sensors 118A, 118B then determine the voltage across or current through the subject S, using the second electrodes 115A, 115B and transfer appropriate signals to the processing system 102.

Accordingly, it will be appreciated that the processing system 102 may be any form of processing system which is suitable for generating appropriate control signals and at least partially interpreting the measured signals to thereby determine the subject's bioelectrical impedance, and optionally determine other information such as relative fluid levels, or the presence, absence or degree of conditions, such as oedema, lymphoedema, measures of body composition, cardiac function, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like, as will be described in more detail below.

In use, the first electrodes 113A, 113B are positioned on the subject to allow one or more signals to be injected into the subject S. The location of the first electrodes will depend on the segment of the subject S under study. Thus, for example, the first electrodes 113A, 113B can be placed on the thoracic and neck region of the subject S to allow the impedance of the chest cavity to be determined for use in cardiac function analysis. Alternatively, positioning electrodes on the wrist and ankles of a subject allows the impedance of limbs and/or the entire body to be determined, for use in oedema analysis, or the like.

Once the electrodes are positioned, one or more alternating signals are applied to the subject S, via the first leads 123A, 123B and the first electrodes 113A, 113B. The nature of the alternating signal will vary depending on the nature of the measuring device and the subsequent analysis being performed.

For example, the system can use Bioimpedance Spectroscopy (BIS) in which impedance measurements are performed at each of a number of frequencies ranging from very low frequencies (4 kHz) to higher frequencies (1000 kHz), and can use as many as 256 or more different frequencies within this range. Such measurements can be performed by applying a signal which is a superposition of plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with each of the signal generators 117A, 117B being independently controllable, to allow the signal voltage across the subject to be varied.

A voltage difference and/or current is measured between the second electrodes 115A, 115B. In one example, the voltage is measured differentially, meaning that each sensor 118A, 118B is used to measure the voltage at each second electrode 115A, 115B and therefore need only measure half of the voltage as compared to a single ended system.

The acquired signal and the measured signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements are determined from the signals to at each frequency by comparing the recorded voltage and the current through the subject. The demodulation algorithm can then produce amplitude and phase signals at each frequency, allowing an impedance value at each frequency to be determined.

As part of the above described process, the distance between the second electrodes 115A, 115B may be measured and recorded. Similarly, other parameters relating to the subject may be recorded, such as the height, weight, age, sex, health status, any interventions and the date and time on which they occurred. Other information, such as current medication, may also be recorded. This can then be used in performing further analysis of the impedance measurements, so as to allow determination of the presence, absence or degree of oedema, to assess body composition, or the like.

The accuracy of the measurement of impedance, can be subject to a number of external factors. These can include, for example, the effect of capacitive coupling between the subject and the surrounding environment, the leads and the subject, the electrodes, or the like, which will vary based on factors such as lead construction, lead configuration, subject position, or the like. Additionally, there are typically variations in, the impedance of the electrical connection between the electrode surface and the skin (known as the "electrode impedance"), which can depend on factors such as skin moisture levels, melatonin levels, or the like. A further source of error is the presence of inductive coupling between different electrical conductors within the leads, or between the leads themselves.

Such external factors can lead to inaccuracies in the measurement process and subsequent analysis and accordingly, it is desirable to be able to reduce the impact of external factors on the measurement process.

One form of inaccuracy that can arise is caused by the voltages across the subject being unsymmetrical, a situation referred to as an "imbalance". Such a situation results in a significant signal voltage at the subject's body centre, which in turn results in stray currents arising from parasitic capacitances between the subject's torso and the support surface on which the subject is provided.

The presence of an imbalance, where the voltage across the subject is not symmetrical with respect to the effective centre of the subject, leads to a "common mode", signal, which is effectively a measure of the signal at the subject. S that is unrelated to the subject's impedance.

To help reduce this effect, it is therefore desirable for signals to be applied to the subject S that they result in a symmetrical voltage about the subject's body centre. As a result, a reference voltage within the subject S, which is equal to a reference voltage of the measurement apparatus, will be close to the effective body centre of the subject, as considered relative to the electrode placement. As the measuring device reference voltage is typically ground, this results in the body centre of the subject S being as close to ground as possible, which minimises the overall signal magnitude across the subject's torso, thereby minimising stray currents.

In one example, a symmetrical voltage about the sensing electrodes cats be achieved by using a symmetrical voltage source, such as a differential bidirectional voltage drive scheme, which applies a symmetrical voltage to each of the drive electrodes 113A, 113B. However, this is not always effective if the contact impedances for the two drive electrodes 113A, 113B are unmatched, or if the impedance of the subject S varies along the length of the subject S, which is typical in a practical environment.

In one example, the apparatus overcomes this by adjusting the differential voltage drive signals applied to each of the drive electrodes 113A, 113B, to compensate for the different electrode impedances, and thereby restore the desired symmetry of the voltages across the subject S. This process is referred to herein as balancing and in one example, helps reduce the magnitude of the common mode signal, and hence reduce current losses caused by parasitic capacitances associated with the subject.

The degree of imbalance, and hence the amount of balancing required, can be determined by monitoring the signals at the sense electrodes 115A, 115B, and then using these signals to control the signal applied to the subject via the drive electrodes 113A, 113B. In particular, the degree of imbalance can be calculated by determining an additive voltage from the voltages detected at the sense electrodes 115A, 115B.

In one example process, the voltages sensed at each of the sense electrodes 115A, 115B are used to calculate a first voltage, which is achieved by combining or adding the measured voltages. Thus, the first voltage can be an additive voltage (commonly referred to as a common mode voltage or signal) which can be determined using a differential amplifier.

In this regard, a differential amplifier is typically used to combine two sensed voltage signals $V_a$, $V_b$, to determine a second voltage, which in one example is a voltage differential $V_a-V_b$ across the points of interest on the subject S. The voltage differential is used in conjunction with a measurement of the current flow through the subject to derive impedance values. However, differential amplifiers typically also, provide a "common mode" signal $(V_a+V_b)/2$, which is a measure of the common mode signal.

Whilst differential amplifiers include a common mode rejection capability, this is generally of only finite effect and typically reduces in effectiveness at higher frequencies, so a large common mode signal will produce an error signal superimposed on the differential signal.

The error caused by common mode signals can be minimised by calibration of each sensing channel. In the ideal case where both inputs of a differential amplifier are perfectly matched in gain and phase characteristics and behave linearly with signal amplitude, the common mode error will be zero. In one example, the two sensing channels of the differential amplifier are digitised before differential processing. It is therefore straightforward to apply calibration factors independently to each channel to allow the characteristics to be matched to a high degree of accuracy, thereby achieving a low common mode error.

Accordingly, by determining the common mode signal, the applied voltage signals can be adjusted, for example by adjusting the relative magnitude and/or phase of the applied signals, to thereby minimise the common mode signal and substantially eliminate any imbalance. An example of this process is described in more detail in copending patent application number WO2009059351.

Figure 2:
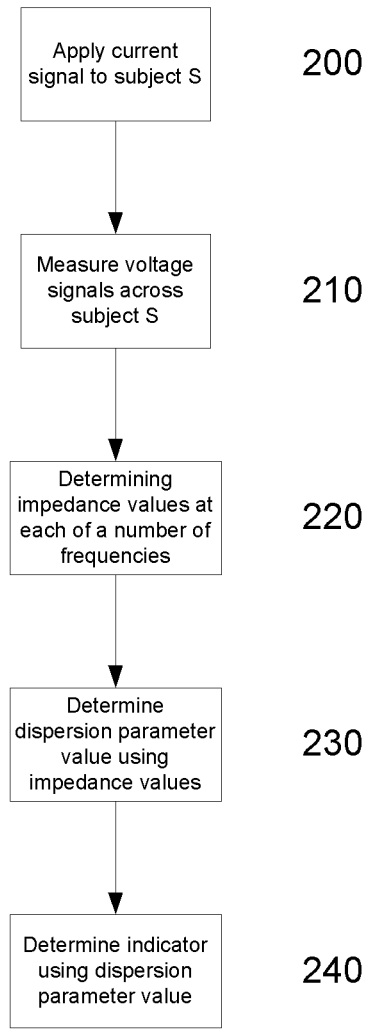
FIG. 2 is a flowchart of an example of a process for determining an indicator.

An example of the operation of the apparatus in analysing impedance measurements will now be described with reference to FIG. 2.

In one example, at step 200 the processing system 102 causes a current signal to be applied to the subject S, with the induced voltage across the subject S being measured at step 210, with signals representing the measured voltage and the applied current being returned to the processing system 102 for analysis.

When the process is being used to determine an oedema indicator, this is typically performed for at least a segment of the subject S that is suspected of being susceptible to oedema, and may also be repeated for a separate healthy segment of the subject. Thus, for example, in the case of limb oedema, this is typically performed on the affected or "at risk" limb (hereinafter generally referred to as the "affected" limb), and a limb that is deemed "not at risk" of oedema (hereinafter generally referred to as the "unaffected" limb).

It will be appreciated that the application of the current and voltage signals may be controlled by a separate processing system that is used in performing the analysis to derive an indicator, and that the use of a single processing system is for the purpose of example only.

At step 220, measured voltage and current signals are used by the processing system 102 to determine impedance values at each of a number of applied frequencies. In one example, this includes first impedance values representing the impedance of the unaffected limb and second impedance values representing the impedance of the affected limb.

At step 230, the one or more impedance values are used by the processing system 102, to determine a dispersion parameter value. In one example, first and second dispersion parameter values of affected and unaffected limbs may be determined.

The nature of the dispersion parameter can vary, but in general this represents a distribution of the impedance measurements about an ideal model.

In one example, the dispersion parameter DP can be given by or based on the value:

$$DP = \frac{X_c}{(R_0 - R_\infty)} \qquad (1)$$

where:
$R_\infty$=impedance at infinite applied frequency;
$R_0$=impedance at zero applied frequency;
$X_c$=reactance at the centre of the circle.

It should be noted that the value of $X_c$ will be negative, due to it's position below the circle, and this can lead to the value of the dispersion parameter being negative. However, it will be appreciated that alternative formulations may also be used, such as those set out below, and accordingly, the dispersion parameter can be arranged to have either a positive or negative value, as desired:

$$DP = \frac{(R_0 - R_\infty)}{X_c} \quad (1A)$$

$$DP = \frac{(R_\infty - R_0)}{X_c} \quad (1B)$$

$$DP = \frac{X_c}{(R_\infty - R_0)} \quad (1C)$$

The alternative formulations can be used to ensure that the value of the dispersion parameter increases in the event that the subject has oedema, although this is not essential and any suitable formulation may be selected.

In one particular example, the dispersion parameter DP value is given by a value $\alpha$:

$$\alpha = \frac{2}{\pi} \arctan \frac{(R_0 - R_\infty)}{2|X_c|} \quad (2)$$

Figure 3A:
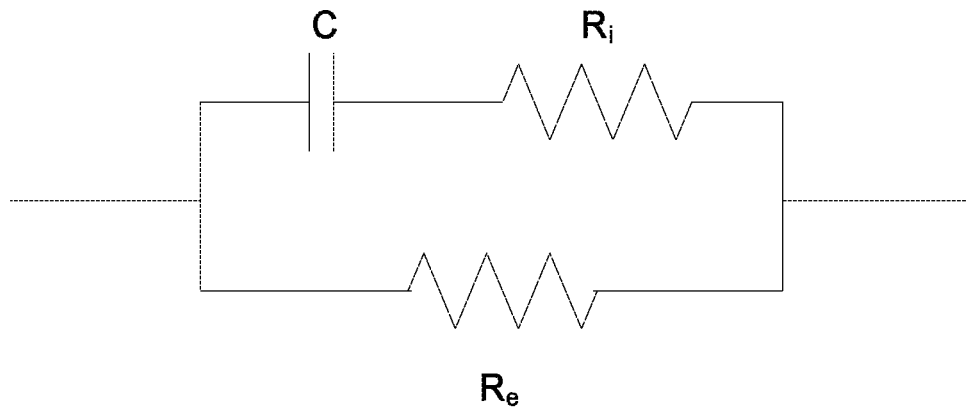
FIG. 3A is a schematic of an example of a theoretical equivalent circuit for biological tissue.

In this regard, FIG. 3A is an example of an equivalent circuit that effectively models the electrical behaviour of biological tissue. The equivalent circuit has two branches that represent current flow through extracellular fluid and intracellular fluid, respectively. The extracellular fluid component of biological impedance is represented by an extra-cellular resistance $R_e$, whilst the intracellular fluid component is represented by an intracellular resistance $R_i$ and a capacitance C representative of the cell membranes.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals the extracellular resistance $R_e$. At infinite frequency the capacitor acts as a perfect conductor and the current passes through the parallel resistive combination. The resistance at infinite frequency $R_\infty$ is given by:

$$R_\infty = \frac{R_e R_i}{R_e + R_i} \quad (3)$$

Accordingly, the impedance of the equivalent circuit of FIG. 3A at an angular frequency $\omega$, where $\omega = 2\pi \ast \text{frequency}$, is given by:

$$Z = R_\infty + \frac{R_0 - R_\infty}{1 + (j\omega\tau)} \quad (4)$$

where:
$R_\infty$ impedance at infinite applied frequency
$R_0$ = impedance at zero applied frequency = $R_e$ and,
$\tau$ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^\alpha} \quad (5)$$

where:
$\alpha$ has a value between 0 and 1 and can be thought of as an indicator of the deviation of a real system from the ideal model.

Figure 3B:
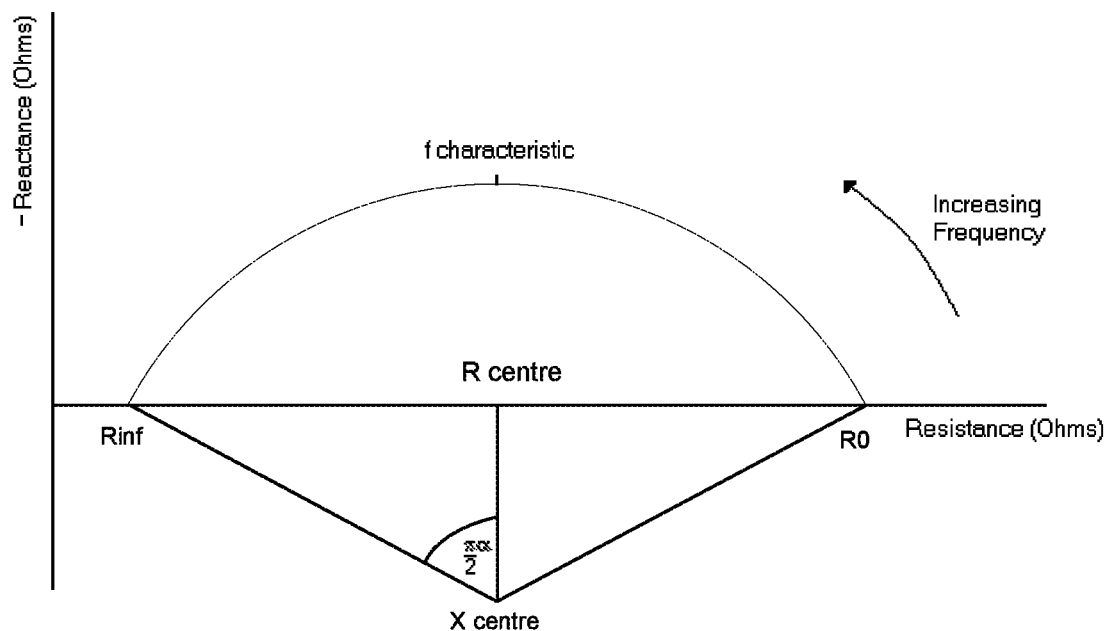
FIG. 3B is an example of a locus of impedance known as a Wessel plot.

An example of the typical multi-frequency impedance response is shown in FIG. 3B. As frequency increases, the reactance increases to a peak and then decreases while the resistance continually decreases. This results in a circular locus with the centre of the circle below the x axis, as shown.

The $\alpha$ parameter is related to the depression of the Cole plot below the zero reactance axis. The value of $\alpha$ is indicative of the deviation from the ideal Cole equation (4) and is closely related to the spectral width of the distribution of relaxation times. This dispersion may be due to molecular interactions, cellular interactions, anisotropy and cell size as described in Grimnes, S. and O. G. Martinsen (2000). Bioimpedance and Bioelectricity Basics, Academic Press.

As described above, the value of the impedance parameter $R_0$ is closely related to extra-cellular fluid levels while the impedance parameter value $R_\infty$ is closely related to the total body fluid levels. Accordingly, $(R_0 - R_\infty)$ is closely related to the intra-cellular fluid levels.

The reactance $X_c$ is the reactance X at the centre of the circle which is a direct measure of the depression of the circular locus below the axis. It is closely related to the reactance at the characteristic frequency by the subtraction from the radius of the locus. At the characteristic frequency, the ratio of the current flow through the intra and extra cellular fluids is determined as a function of the ratio of the intra to extra cellular resistance, so that it is independent of the capacitance of the cell membrane. Accordingly, the reactance at the characteristic frequency can be used more accurately as an indicator of extra-cellular fluid levels. Since the reactance at the centre of the circle is directly related to the characteristic reactance, this value is also related to the intra and extra cellular fluid.

Accordingly, the dispersion parameter is not only related to a ratio of extra-cellular to intra-cellular fluid levels, but also takes into account deviation from an idealised equivalent circuit reflecting the distribution of relaxation times within the subject and so encompasses changes in cell structure. In contrast, if a direct ratio of intra-cellular to extra-cellular fluid is used as an index I this is typically calculated as shown in equation (6) below and therefore does not account for such deviations to the same extent.

$$I = \frac{R_i}{R_e} = \frac{R_\infty}{R_0 - R_\infty} \quad (6)$$

As lymphoedema is characterised by the accumulation of extra-cellular fluid, the dispersion parameter is different between a healthy and oedema affected population, with the difference being more readily quantifiable than if a direct ratio of intra-cellular to extra-cellular, given by equation (6) is used.

An example of the propagation of errors in the calculation of a dispersion parameter alpha and a ratio of intra-cellular to extra-cellular fluid will now be described. In order to determine the propagation of errors, it is necessary to take into account typical measurement errors in different frequency ranges for a typical measurement device, and these are shown in Table 1 below.

TABLE 1

| Frequency Range | Body Impedance | Impedance Error | Phase Error |
| --- | --- | --- | --- |
| 3-100 kHz | 200-1100 Ohms | +/−1% | +/−1% |
| 100-1000 kHz | 200-1100 Ohms | +/−2% | +/−2% |

In this instance, the relative error in the index I from equation (6) is given by:

$$\frac{\Delta I}{I'} = \frac{\Delta R_\infty}{R_\infty} + \frac{\Delta R_0 + \Delta R_\infty}{R_0 + R_\infty}$$

Similarly the relative error in the indicator Ind from equation (1) is given by:

$$\frac{\Delta Ind}{Ind} = \frac{\Delta X_C}{X_C} + \frac{\Delta R_0 + \Delta R_\infty}{R_0 - R_\infty}$$

Given the typical errors specifications for the measuring devices outlined in Table 1 above, and taking example leg impedance measurements, this leads to example impedance parameter values of:

$R_0 = 372\Omega \pm 1\%$ $R_\infty = 25\Omega \pm 2\%$ $X_C = -28\Omega \pm 1\%$ Accordingly, this leads to errors of:

$$\frac{\Delta I}{I} = 2 + \frac{0.01 \cdot 372 + 0.02 \cdot 253}{372 + 253} = 2.01\%$$

$$\frac{\Delta Ind}{Ind} = 1 + \frac{0.01 \cdot 372 + 0.02 \cdot 253}{372 - 253} = 1.07\%$$

This demonstrates that the alpha parameter can be determined more accurately and should therefore be more sensitive to fluid level changes within the subject, and hence the presence absence or degree of oedema.

At step 240, the dispersion parameter can be used to determine an indicator. In one example; the indicator provides information relating to the subject, such as an indication of fluid levels within the subject. In one example, the indicator is in the form of a numerical value that depends on a reference, and which can be used to determine the presence, absence or degree of a condition, such as oedema.

In one particular example, the reference is at least partially based on the dispersion parameter of an unaffected body segment. In particular, if the affected body segment does not in fact have oedema, then the dispersion parameter will be similar to the dispersion parameter for the unaffected body segment, thereby minimising a difference between first and second dispersion parameters. In contrast if the affected body segment has oedema the fluid levels will differ to the fluid levels in the unaffected body segment, meaning that the difference between the first and second dispersion parameters increases. As a result, the magnitude of the difference in first and second dispersion parameters between first and second body segments can be indicative of the presence, absence or degree of oedema. Accordingly, by comparing the difference between the dispersion parameters of affected and unaffected body segments to a threshold amount, then this can therefore be used to determine the presence, absence or degree of oedema.

In one example, the difference is scaled by a scaling factor so that the indicator and the threshold can be a memorable value, such as an integer value, or the like. This can be achieved by calculating an indicator as follows:

$$Ind = sf(DP_2 - DP_1) \quad (7)$$

where:

Ind is the indicator $DP_1$ is the first dispersion parameter value of the affected body segment $DP_2$ is the second dispersion parameter value of the unaffected body segment sf is a scaling factor However, a population study of healthy subjects has found inherent differences in fluid levels between different body segments, such as limbs, even in unaffected individuals. This can include slight differences in dispersion parameters due to limb dominance in limbs as well as differences arising if the unaffected and affected limbs are of different limb types, such as arms and legs. For example, the dispersion parameter for a subject's leg will typically differ to that of the subject's arm, even in the absence of oedema in both limbs.

Accordingly, when calculating the reference it is typical to determine a predicted dispersion parameter value for the affected limb based on the second dispersion parameter value determined for the unaffected limb. This is usually achieved using at least one reference value derived from a reference normal population, allowing the natural variations between limbs due to gender, limb dominance and different limb types to be accommodated.

In one particular example, the predicted dispersion parameter value is calculated based on parameters derived by performing a linear regression of first and second dispersion parameter values measured for a reference population. The predicted dispersion parameter value can then be determined using an equation of the form:

$$DP_p = aDP_2 + K \quad (8)$$

where:

$DP_2$ is the second dispersion parameter value $DP_p$ is the predicted dispersion parameter value a is a multiplier reference value determined based on a relationship between first and second dispersion parameter values for a reference population K is a constant reference value determined based on a relationship between first and second dispersion parameter values for the reference population In one example, for a male subject, the predicted value for a leg segment based on second dispersion parameters for an arm segment is based on a value of a in the range 0.15 to 0.022, and a value of K in the range 0.62 to 0.72. For a female subject, the predicted value for a leg segment based on second dispersion parameters for an arm segment is based on a value of a in the range 0.44 to 0.41, and a value of K in the range 0.43 to 0.46.

When a predicted dispersion parameter value is used, the indicator can be determined using the equation:

$$Ind = \frac{sf \times (DP_p - DP_1)}{3SE} \quad (9)$$

where:
Ind is the indicator
$DP_1$ is a dispersion parameter value determined for the body segment
$DP_p$ is a predicted dispersion parameter value for the body segment
sf is a scaling factor
SE is a standard error determined based on dispersion parameter values in a reference population It should be noted that in the event that measurements are made for an affected body segment only, then the predicted dispersion parameter value could alternatively be based on a mean value obtained from a reference population, leading to an indicator of the form:

$$Ind = \frac{sf \times (DP_\mu - DP_1)}{3SE} \quad (10)$$

where:
$DP_\mu$ is the mean dispersion parameter value for a reference normal population
sf is a scaling factor
SE is a standard error determined based on dispersion parameter values for the reference population Accordingly, it will be appreciated that the above described dispersion parameter can be used in diagnosing the presence, absence or degree of oedema. Furthermore, in contrast to prior art techniques, a dispersion parameter tends to provide more reliable results, as will be discussed in more detail below.

In the above examples, it will be appreciated that the order of the dispersion parameters could be reversed, so that for example in equation (9) the predicted value could be subtracted from the measured value and this will depend on the nature of the dispersion parameter used, so for example whether the dispersion parameter is based on equations (1), (1A), (1B), (1C), (2), or variations thereof. In general the order used will be selected so that the indicator Ind increases in magnitude as the level of oedema increases, however this is not essential and any suitable arrangement may be used.

Figure 4:
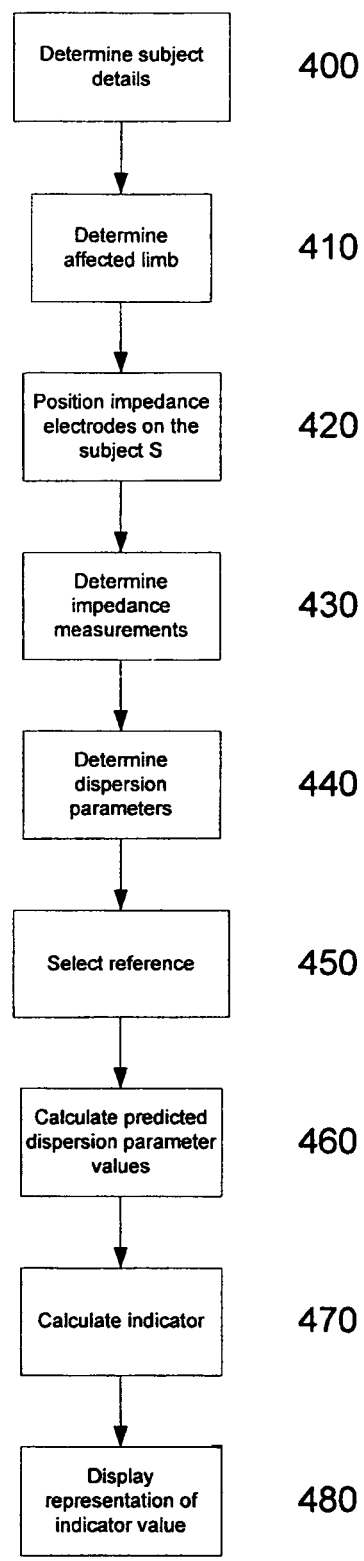
FIG. 4 is a flowchart of an example of a process for determining an oedema indicator for limb oedema.

An example of the process for performing impedance measurements to determine an indicator for limb oedema will now be described in more detail with reference to FIG. 4.

In this example, at step 400 subject details are determined and provided to the processing system 102. The subject details will typically include information such as limb dominance, details of any medical interventions, as well as information regarding the subject such as the subject's age, weight, height, sex, ethnicity or the like. The subject details can be used in selecting a suitable reference normal population, as well as for generating reports, as will be described in more detail below.

It will be appreciated that the subject details may be supplied to the processing system 102 via appropriate input means, such as the I/O device 105. Thus, each time a subject measurement is performed this information can be input into the measuring device 100.

However, more typically the information is input a single time and stored in an appropriate database, or the like, which may be connected as a peripheral device 104 via the external interface 103. The database can include subject data representing the subject details, together with information regarding previous oedema indicators, baseline measurements or impedance measurements recorded for the subject.

In this instance, when the operator is required to provide subject details, the operator can use the processing system 102 to select a search database option allowing the subject details to be retrieved. This is typically performed on the basis of a subject identifier, such as a unique number assigned to the individual upon admission to a medical institution, or may alternatively be performed on the basis of name or the like. Such a database is generally in the form of an HL7 compliant remote database, although any suitable database may be used.

In one example, the subject can be provided with a wristband or other device, which includes coded data indicative of the subject identifier. In this case, the measuring device 100 can be coupled to a peripheral device 104, such as a barcode or RFID (Radio Frequency Identification) reader allowing the subject identifier to be detected and provided to the processing system 102, which in turn allows the subject details to be retrieved from the database. The processing system 102 can then display an indication of the subject details retrieved from the database, allowing the operator to review these and confirm their accuracy before proceeding further.

At step 410 the affected limb, or "at risk" limb, is determined. This may be achieved in any one of a number of ways depending on the preferred implementation. Thus, for example, the affected limb can be indicated through the use of appropriate input means, such as the I/O device 105. Alternatively this information can be derived directly from the subject details, which, may include an indication of the affected limb, or details of any medical interventions performed, which are in turn indicative of the affected limb.

At step 420 an operator positions the electrodes on the subject S, and connects the leads 123, 124, 125, 126, to allow the impedance measurements to be performed. The general arrangement is to provide electrodes on the hand at the base of the knuckles and between the bony protuberances of the wrist, as shown in FIG. 5A, and on the feet at the base of the toes and at the front of the ankle, as shown in FIG. 5B. The configurations shown in FIGS. 5C and 5D allow the right arm 531 and the right leg 533 to be measured respectively, and it will be appreciated that equivalent arrangements can be used to measure the impedance of the left leg and left arm.

It will be appreciated that this configuration uses the theory of equal potentials, allowing the electrode positions to provide reproducible results for impedance measurements. For example when current is injected between electrodes 113A and 113B in FIG. 5C, the electrode 115B could be placed anywhere along the left arm 532, since the whole arm is at an equal potential.

This is advantageous as it greatly reduces the variations in measurements caused by poor placement of the electrodes by the operator. It also greatly reduces the number of electrodes required to perform segmental body measurements, as well as allowing the limited connections shown to be used to measure each limb separately.

However, it will be appreciated that any suitable electrode and lead arrangement may be used.

At step 430 the impedance of the affected and unaffected limbs are measured. This is achieved by applying one or more current signals to the subject and then measuring the corresponding voltages induced across the subject S. It will be appreciated that in practice the signal generators 117A, 117B, and the sensors 118A, 118B, return signals to the processing system 102 indicative of the applied current and the measured voltage, allowing impedances to be determined.

Following at step 440 a dispersion parameter DP for each of the limbs is determined using equations (1) or (2) above.

At step 450 a reference is selected. The reference is typically derived from equivalent measurements made on a normal population (subject's not suffering from oedema) that is relevant to the subject under study. Thus, the normal population is typically selected taking into account factors such as medical interventions performed, ethnicity, sex, height, weight, limb dominance, the affected limb, or the like.

Therefore if the test subject is female having bilateral lymphoedema of the dominant leg then the normalised data drawn from the normal population database will be calculated from the dominant leg impedance ratio measurements from female subjects that are present in the normal population database.

Accordingly, at this stage the processing system 102 typically accesses reference populations stored in the database, or the like. This may be performed automatically by the processing system 102 using the subject details. Thus for example, the database may include a look-up table that specifies the normal population that should be used given a particular set of subject details. Alternatively selection may be achieved in accordance with predetermined rules that can be derived using heuristic algorithms based on selections made by medically qualified operators during previous procedures. Alternatively, this may be achieved under control of the operator, depending on the preferred implementation.

It will be appreciated by persons skilled in the art that operators may have their own reference stored locally. However, in the event that suitable references are not available, the processing system 102 can be used to retrieve a reference from a central repository, for example via an appropriate server arrangement. In one example, this may be performed on a pay per use basis.

Alternatively, in the event that a suitable reference is not available predetermined standard reference values may be used, as described above. However it will be appreciated that different values can be used as appropriate and that these values are for illustration only.

At step 460 a predicted dispersion parameter value for the affected body segment is determined using the second dispersion value derived for the unaffected body segment and the reference values, as described above with respect to equation (8).

Following this an indicator can be determined using equation (9) at step 470. As described above, this is typically achieved by scaling the difference between the predicted and measured dispersion parameter values for the affected arm. This is performed so that the value of the indicator at a threshold indicative of the presence of oedema corresponds to a memorable value. In one example, the scaling factor is set so that an indicator value of greater than "10" is indicative of oedema, whilst a value of below "10" is used to indicate an absence of oedema.

Representations of the indicator can then optionally be displayed at step 480. Examples of such representations for oedema indicators will now be described with reference to FIGS. 6A and 6B.

In these examples, the representation is in the form of a linear indicator 600, having an associated scale 601 and a pointer 602. The position of the pointer 602 relative to the scale 601 is indicative of the subject parameter, which in this example is based on an impedance ratio representing a ratio of fluid levels determined for healthy and affected limbs of the subject.

Figure 6A:
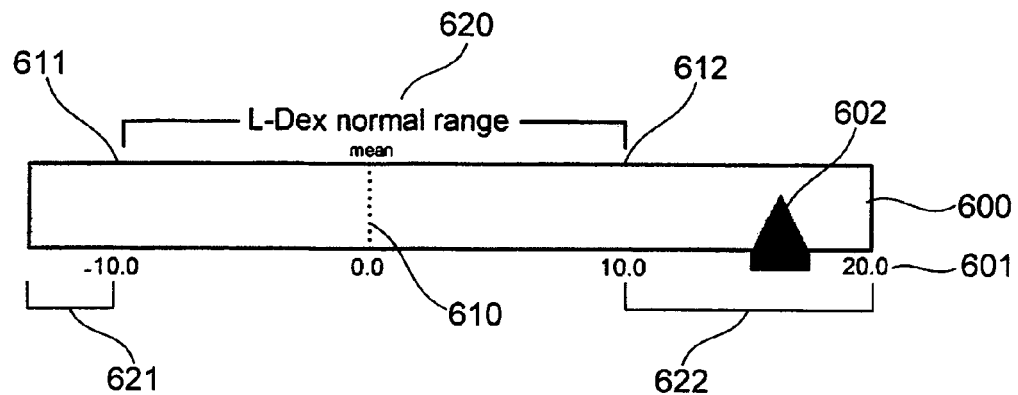
FIG. 6A to 6C are schematic diagrams of first examples of representations of oedema indicators.

In the example of FIG. 6A, the indicator representation also includes a mean indicator 610 representing the mean indicator for the normal population, which is set to a value of "0" on the scale 601. The upper and lower thresholds are set to be three standard deviations from the mean 610, and are set to be positioned at "−10" and "+10" on the scale 601 respectively.

In use the lower and upper thresholds 611, 612 define a normal range 620, an investigation range 621, and an oedema range 622. The ranges can be indicated through the use of background colours on the linear indicator, so that for example, the normal range 620 is shaded green, whilst the investigation range 621 is unshaded, and the oedema range 622 is shaded red. This allows an operator to rapidly evaluate the positioning of the pointer 602 within the ranges, allowing for fast and accurate diagnosis of oedema based on the indicated fluid level information.

Thus, in the example of FIG. 6A, the pointer 602 is positioned at the value of 16.6, placing the pointer 602 in the oedema range 622, indicating to the user that the fluid levels in the subject S are probably indicative of oedema in the affected limb.

In this example, the linear indicator extends up to a value of "20" as this is able to accommodate the determined value of 16.6. However, it will be appreciated that the linear indicator can be extended to any value required to accommodate the determined indicator value. To ensure that the linear scale remains clear, particularly if an extreme indicator value is to be displayed, the linear indicator 600 may include discontinuities, allowing the scale to be extended to higher values. An example of this is shown in FIG. 6C, in which a discontinuity 605 is used to separate the linear indicator 600 into two portions 600A, 600B. In this example, the linear indicator portion 600A extends from "−10" to "+20", whilst the second linear indicator portion 600B extends from "+70" to "+90", thereby allowing an indicator value of "80" is to be displayed by appropriate positioning of the pointer 602 in the indicator portion 605B.

Whilst a linear indicator 600 is preferred as this easily demonstrates to the operator the potential degree of severity of any oedema, this is not essential, and alternatively the scale may be modified, particularly if an outlier indicator value is determined. Thus, for example, the linear indicator could include logarithmic scaling, or the like, over all or part of its length, to allow the determined indicator value to be displayed.

In the event that the indicator value is between "−10" and "+10", this indicates that the subject S is within the normal range 620 and that therefore they do not have oedema. Finally, in the event that the indicator value is below "−10", then the subject S is within the investigation range 621, indicating that the measurements need to be investigated further. In particular, it is extremely unlikely that, the affected limb could have an impedance value significantly smaller than that of the unaffected limb, and accordingly, this indicates that in all likelihood there has been an error in the measurement, such as incorrect designation of the affected limb, or incorrect connection of electrodes.

Figure 6B:
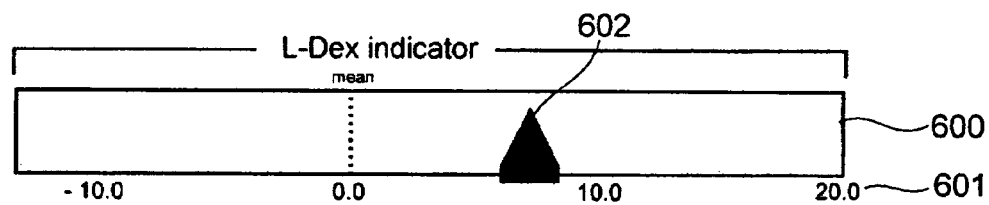
Figure 6C:
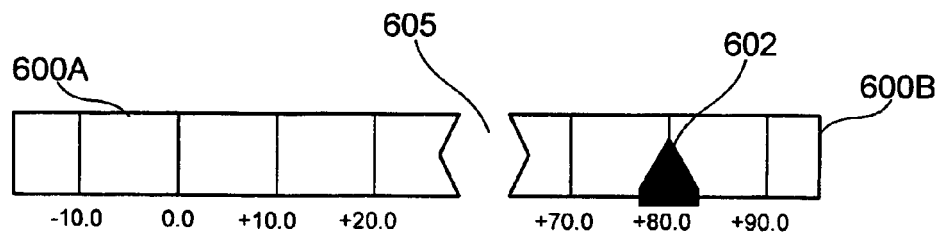

In the example of FIG. 6B, no reference is available, and accordingly, the representation does not includes a mean 610 or lower or upper thresholds 611, 612. In this instance, the indicator value is still scaled using default standard values. This may be used if the indicator is determined based on equation (7).

As a result an oedema indicator value of above "10" is still indicative of oedema, but may be a less reliable indicator than if the reference is available. To take this into account, the thresholds 611, 612, and hence the specific ranges 620, 621, 622, are excluded from the representation, highlighting to the operator that the scaled subject parameter value is indicative but not definitive of the subject's oedema status.

Experimental Examples

A survey of the normal population was conducted using an Impedimed SFB7 device to determine the "normal" values for the Cole parameters. 65 self diagnosed healthy females and 29, self diagnosed healthy males participated in a trial with the population demographics being shown in Table 2. The average and standard deviation of the Cole parameters for each limb was determined for both the dominant and non dominant limbs.

TABLE 2

|  | Male | Female |
| --- | --- | --- |
| Age (years) μ(σ) | 40.1 (13.2) | 42.6 (11.7) |
| Height (cm) μ(σ) | 179.6 (7.5) | 162.6 (21.3) |
| Weight (kg) μ(σ) | 86.6 (16.9) | 69.4 (16.9) |

Of the single Cole parameters, a is the parameter that has the lowest variation for all limbs within a normal population (COV=1-3%), thereby indicating that this is generally a more consistent parameter for healthy individuals.

The variation of some combinations of the Cole parameters was also investigated. The parameters with the lowest coefficient of variation in a control population were $R_0/R_\infty$, $R_0/X_c$. $R_i/R_e$ has a large coefficient of variation (10-15%) which suggests that this would make it difficult to use this impedance ratio to successfully distinguish between inherent variations within a subject, and variations induced by the presence of oedema or lymphoedema.

The normal arm to leg ratio calculated from the reference data for the same Cole parameters again results in the parameters having the lowest variation (<5%) being α, $R_0/R_\infty$ and $R_0/X_c$.

To evaluate a bilateral approach, leg data from leg lymphoedema sufferers was obtained. Data was collected during a clinical trial in which 30 volunteers were invited to participate. Each subject was classified into the Control, Bilateral Lymphoedema or Unilateral Lymphoedema group based on provided medical history. Subjects were required to lie in a supine position while electrodes were attached to the hands and feet using standard placement markers. Three swept frequency bioimpedance measurements of each limb were recorded.

The population demographics are shown in Table 3 for the subjects who met eligibility criteria. The mean subject age was significantly higher than for the normal data previously collected in a healthy population. The mean heights for both trials are comparable and the mean weight for the control subjects was comparable to the normal data collected previously. However the unilateral and bilateral subjects recorded higher weights. This is to be expected as the amount of fluid in a leg affected by lymphoedema will contribute to the weight.

TABLE 3

|  | Control (M/F) | Unilateral (M/F) | Bilateral (M/F) |
| --- | --- | --- | --- |
| Gender | 4/6 | 3/8 | 4/4 |
| Age (years) μ(σ) | 59.3 (4.0)/48.5 (21.6) | 61.4 (12.5)/59.1 (13.1) | 63.0 (14.6)/65.8 (11.8) |
| Height (cm) μ(σ) | 179.8 (2.4)/165.5 (6.7) | 180.7 (4.0)/161.9 (10) | 177.5 (6.9)/163.5 (5.3) |
| Weight (kg) μ(σ) | 84.8 (3.8)/65.8 (11.1) | 89.3 (10.2)/75.4 (15.2) | 123.0 (31.1)/93.5 (24.8) |

A review of the COV in Table 2 suggests that other parameters other than $R_i/R_e$ are more stable within a normal population. These are the $R_0/R_\infty$, $Ro/X_c$ and α parameters.

An indicator was derived for each single limb from the $R_0/R_\infty$, $Ro/X_c$ and α parameters. The results for an indicator calculated based on α are shown in table 46, using a reference from a standard population. The indicator is calculated for each limb independently using a reference value for a obtain from the reference normal population, as shown in equation (10).

TABLE 4

| Subject No | Gender | Group | Ind Dom Arm | Ind Non Dom Arm | Ind Dom Leg | Ind Non Dom Leg |
| --- | --- | --- | --- | --- | --- | --- |
| UB500-01-01 | Female | Control | 0.8 | −0.1 | −2.0 | −1.3 |
| UB500-01-09 | Female | Control | −2.3 | −3.0 | −6.2 | −5.4 |
| UB500-01-13 | Female | Control | −3.5 | −0.6 | −6.4 | −6.5 |
| UB500-01-14 | Female | Control | −7.8 | −5.8 | −7.5 | −9.1 |
| UB500-01-24 | Female | Control | −5.7 | −2.3 | −9.6 | −7.4 |
| UB500-01-25 | Female | Control | 2.3 | 3.3 | −5.5 | −1.7 |
| UB500-01-02 | Male | Control | −1.2 | −0.1 | −3.8 | −4.2 |
| UB500-01-17 | Male | Control | −6.7 | −11.5 | −8.7 | −11.0 |
| UB500-01-23 | Male | Control | −6.0 | −2.8 | −9.0 | −5.2 |
| UB500-01-29 | Male | Control | 1.7 | 6.5 | −7.3 | −2.6 |
| UB500-01-04 | Female | Uni | −3.4 | −1.0 | −7.6 | −15.2 |
| UB500-01-05 | Female | Uni | −2.7 | −6.3 | −7.6 | −15.0 |
| UB500-01-12 | Female | Uni | −3.9 | −3.4 | −14.4 | −7.4 |
| UB500-01-15 | Female | Uni | 0.4 | 0.1 | −10.4 | −29.8 |
| UB500-01-22 | Female | Uni | −9.0 | −4.9 | −16.8 | −13.8 |
| UB500-01-26 | Female | Uni | −0.4 | −1.4 | −16.3 | −11.9 |
| UB500-01-28 | Female | Uni | −2.1 | 1.7 | −10.0 | −4.9 |
| UB500-01-08 | Male | Uni | 0.3 | 4.9 | −15.0 | −0.4 |
| UB500-01-18 | Male | Uni | −0.2 | 1.3 | −16.9 | −10.2 |
| UB500-01-03 | Female | Bi | −3.3 | −1.2 | −8.6 | −8.6 |
| UB500-01-07 | Female | Bi | −3.2 | −1.8 | −23.6 | −27.3 |
| UB500-01-11 | Female | Bi | −11.1 | −12.3 | −19.7 | −21.2 |
| UB500-01-19 | Female | Bi | −5.2 | −6.5 | −34.9 | −26.3 |
| UB500-01-06 | Male | Bi | 0.6 | 5.5 | −27.6 | −32.2 |
| UB500-01-10 | Male | Bi | −20.0 | −28.4 | −27.5 | −24.1 |
| UB500-01-20 | Male | Bi | −7.4 | −22.7 | −26.2 | −19.9 |
| UB500-01-27 | Male | Bi | −1.7 | 2.6 | −22.8 | −20.0 |

In this example, the indicator values are negative as the reference dispersion parameter was subtracted from the measured value (the reverse situation to that shown in equation (10)) and as a decreases with an increase in lymphoedema. In this example, the scaling factor is selected so that −10 is an indication of lymphoedema.

Table 5 shows the specificity and sensitivity of the dispersion parameter α in being indicative of the presence of lymphodema. These results are greatly improved compared to using an $R_i/R_e$ ratio for each limb. It should be noted that the sensitivity of the arms cannot be calculated as no affected arms were measured.

TABLE 5

|  | Dom Arm | Non Dom Arm | Dom Leg | Non Dom Leg |
|---|---|---|---|---|
| Specificity (%) | 93 | 85 | 80 | 86 |
| Sensitivity (%) | n/a | n/a | 92 | 92 |

The biggest concern for this approach is the high indicator value recorded for three of the arms of the subjects. It would be expected that the indicator calculated for these unaffected arms would be within the normal range. In addition, the positive assessment of lymphoedema in some of the unaffected legs of the unilateral subjects may not be a false positive, but rather a sign that the lymphoedema is present in both legs.

The results highlight the ability to assess the presence of lymphoedema from the measurement of a single affected limb, meaning that this allows a technique to be implemented that requires only a single measurement of the affected limb.

Arm to leg ratios that resulted in a low coefficient of variation were again $R_0R_\infty$, $R_0/X_c$ and $\alpha$. From these, an indicator was calculated for the dominant and non dominant leg from the arm to leg ratios, similar to equation (7). The parameter that showed the greatest effectiveness is the ratio of arm to leg for the dispersion parameter $\alpha$. Table 6 shows the specificity and sensitivity using this method is still low.

TABLE 6

|  | Dom Leg | Non Dom Leg |
|---|---|---|
| Specificity (%) | 87 | 93 |
| Sensitivity (%) | 42 | 54 |

The above results suggest that perhaps the relationship between the arm and leg is not a one to one relationship. The ratio of affected to unaffected limb approach works well with unilateral lymphoedema as the affected limb is compared to an equivalent but contra-lateral limb. The ratio of unaffected limb to affected limb is very close to 1. This is the equivalent of assuming a linear relationship between the limbs without a constant offset. That is y=mx+c without the intercept c and where m is the normal ratio.

Figure 7:
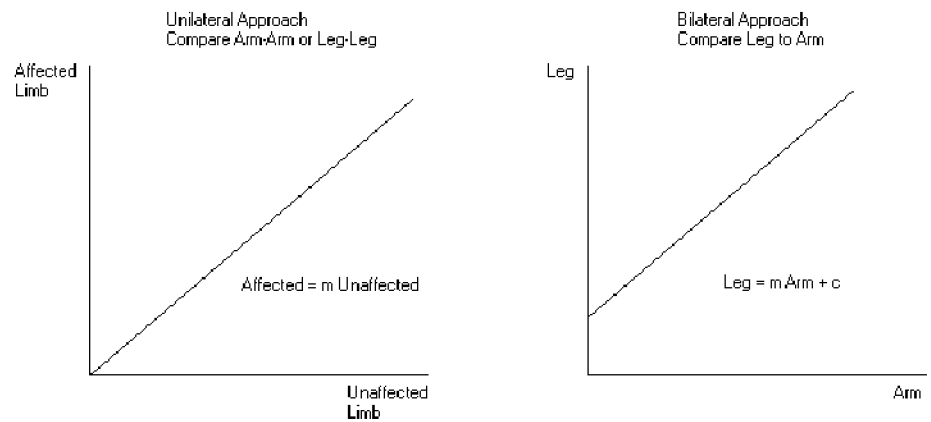
FIG. 7 are graphs of examples of the relationship of parameters between like limbs and dislike limbs; and,
FIG. 8 is a graph of example measurements of leg α and arm α for healthy female dominant arms and legs.

In essence this uses the healthy limb to predict what we would expect the affected limb to be if it were also unaffected. The deviation of the expected result from the measured result is then compared to the normal variation within a healthy population to assess the presence of lymphoedema. In the case of comparing an arm to a leg, there are a number or differences in geometry and structure such as cross sectional area and length. This would indicate an additional offset between the two measurements and suggest that the relationship between arms and legs may be linear. These concepts are shown graphically in FIG. 7.

Figure 8:
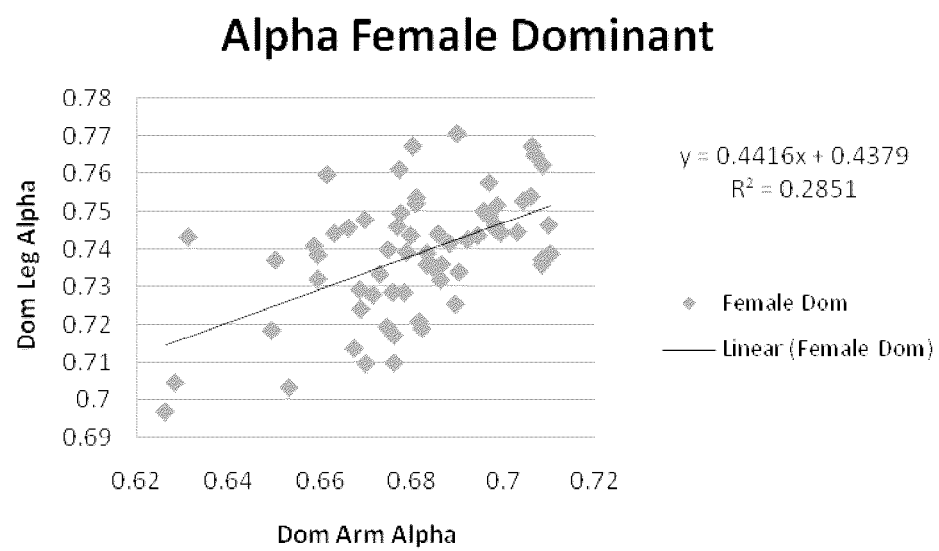

An example of the variation of a normal leg $\alpha$ with normal arm $\alpha$ is shown for dominant arms and legs for healthy females in FIG. 8. This data is collected using the ImpediMed SFB7. No outliers have been rejected in this instance.

Regression analysis was performed on the healthy male and female, dominant and non dominant limb data to determine the line of best fit for the chosen parameters. The female normal data shows a stronger association (R>0.5) than the male data (R=0.2) for all parameters.

The resulting linear equations used to predict leg data from arm data are grouped by gender and dominance. The best performing parameter is $\alpha$. The equations are shown below.

Female Dominant: $\alpha_{leg}=0.4416\alpha_{arm}+0.4379$, SE=0.0136

Female Non Dominant: $\alpha_{leg}=0.4176\alpha_{arm}+0.4581$, SE=0.0136

Male Dominant: $\alpha_{leg}=0.1572\alpha_{arm}+0.6227$, SE=0.0113

Male Non Dominant: $\alpha_{leg}=0.0217\alpha_{arm}+0.7145$, SE=0.0109

These regression equations were then used to predict the expected leg $\alpha$ from the measured arm $\alpha$, using equation (8) above. Next the predicted leg $\alpha$ was subtracted from the measured leg $\alpha$. This difference between the actual and predicted result was then compared to the standard error for a normal population. An indicator value was calculated according to equation (9).

Example results for leg $\alpha$ predicted from arm measurements are shown in Table 7.

TABLE 7

| Subject No | Gender | Group | indicator Dom Leg | Indicator Non Dom Leg |
|---|---|---|---|---|
| UB500-01-01 | Female | Control | 2.8 | 1.5 |
| UB500-01-09 | Female | Control | 7.4 | 6.4 |
| UB500-01-13 | Female | Control | 5.2 | 7.3 |
| UB500-01-14 | Female | Control | 3.9 | 6.8 |
| UB500-01-24 | Female | Control | 7.6 | 7.3 |
| UB500-01-25 | Female | Control | 2.4 | 5.4 |
| UB500-01-02 | Male | Control | 6.5 | 3.9 |
| UB500-01-17 | Male | Control | 6.8 | 7.5 |
| UB500-01-23 | Male | Control | 6.9 | 6.0 |
| UB500-01-29 | Male | Control | 9.4 | 3.0 |
| UB500-01-04 | Female | Uni | 6.7 | 17.4 |
| UB500-01-05 | Female | Uni | 7.2 | 13.5 |
| UB500-01-12 | Female | Uni | 19.7 | 8.5 |
| UB500-01-15 | Female | Uni | 12.3 | 35.3 |
| UB500-01-22 | Female | Uni | 14.1 | 13.0 |
| UB500-01-26 | Female | Uni | 16.7 | 21.2 |
| UB500-01-28 | Female | Uni | 16.0 | 28.5 |
| UB500-01-08 | Male | Uni | 10.3 | 7.1 |
| UB500-01-18 | Male | Uni | 14.5 | 4.5 |
| UB500-01-03 | Female | Bi | 8.0 | 9.5 |
| UB500-01-07 | Female | Bi | 32.8 | 37.6 |
| UB500-01-11 | Female | Bi | 16.2 | 16.8 |
| UB500-01-19 | Female | Bi | 48.7 | 36.0 |
| UB500-01-06 | Male | Bi | 24.9 | 30.5 |
| UB500-01-10 | Male | Bi | 15.4 | 13.5 |
| UB500-01-20 | Male | Bi | 27.5 | 20.3 |
| UB500-01-27 | Male | Bi | 24.4 | 20.6 |

These results highlight that the use of the dispersion parameter $\alpha$ together with the prediction of an expected value for the affected limb based on measurements for the unaffected limb provide a high reliability of identification of lymphoedema as highlighted by sensitivity and specificity measures shown in Table 8. Of all methods presented, the results demonstrate the highest specificity and sensitivity.

TABLE 8

|  | Dom Leg | Non Dom Leg |
|---|---|---|
| Specificity (%) | 80 | 93 |
| Sensitivity (%) | 92 | 92 |

It should be noted that Bilateral subject UB500-01-03 did not record an indicator of greater than 10. This can be explained as the subject had a very mild case of lymphoedema affecting only the upper most part of the thigh. It is expected that the contribution of the lymphoedema to the measured bioimpedance was not significant to be greatly altered from the normal state. However it will be noticed that in both legs an indicator score was, obtained that was greater than 8.

The remaining unilateral subjects whose unaffected leg produced an indicator of greater than 10, are potentially showing signs of developing lymphoedema in the other leg.

Accordingly, this highlights that using a dispersion parameter has been shown to produce the best results in predicting the presence of lymphoedema.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used for determining the health status of an individual, including the body composition of the individual, or diagnosing the presence, absence or degree of a range of conditions and illnesses, including, but not limited to oedema, lymphoedema, or the like. It will be appreciated from this that whilst the above examples use the term oedema indicator, this is for the purpose of example only and is not intended to be limiting. Accordingly, the oedema indicator can be referred to more generally as an indicator when used in analysing impedance measurements with respect to more general health status information such as body composition, or the like.

The claims defining the invention are as follows:

1. A method for use in diagnosing a presence, absence or degree of oedema in a subject suspected of having the oedema by using impedance measurements performed on the subject, the method being performed using an apparatus including:
    a first set of electrodes for applying to the subject;
    a signal generator for applying excitation electrical signals to the subject using the first set of electrodes;
    a second set of electrodes for applying to the subject;
    a sensor for measuring measured electrical signals across the second set of electrodes; and,
    a processing system including at least one of a programmable computer system or a field-programmable gate array,
    the method including, in the processing system:
    causing the impedance measurements to be performed by:
        causing the excitation electrical signals to be applied to the subject using the signal generator;
        determining the measured electrical signals across the subject using the sensor; and,
        determining, using an indication of the excitation electrical signals and an indication of the measured electrical signals, impedance values at each of a number of frequencies for first and second body segments of the subject, each impedance value representing an impedance of the respective body segment, wherein the first body segment is a body segment of the subject that is suspected of being affected by the oedema and the second body segment is a body segment of the subject that is suspected of being unaffected by the oedema;
    determining impedance parameter values for the first and second body segments based on the impedance values for the respective body segment, the impedance parameter values including:
        $R_\infty$ representing an impedance at infinite applied frequency;
        $R_0$ representing an impedance at zero applied frequency; and,
        $X_c$ representing a reactance at a centre of a circle defined by the impedance values for the respective body segment;
    determining first and second dispersion parameter values for the first and second body segments respectively, each dispersion parameter value being indicative of a dispersion of the impedance values for the respective body segment, each dispersion parameter value being based on a ratio of:
        a difference between $R_\infty$ and $R_0$ for the respective body, and,
        $X_c$ for the respective body segment;
    determining an indicator using the first and the second dispersion parameter values; and,
    displaying a representation of the indicator, to thereby allow the presence, the absence or the degree of the oedema in the subject to be diagnosed.

2. A method according to claim 1, wherein at least one of the first and second body segments is a dominant limb and the other of the first and second body segments is a non-dominant limb.

3. A method according to claim 1, wherein the method includes, in the processing system:
    determining a predicted dispersion parameter value for the first body segment using the second dispersion parameter value; and,
    determining the indicator using the first and predicted dispersion parameter values.

4. A method according to claim 3, wherein the predicted dispersion parameter value is determined to take into account at least one of:
    limb dominance; and,
    differences in limb types.

5. A method according to claim 3, wherein the method includes, in the processing system, determining the predicted dispersion parameter value using at least one reference value derived from a reference normal population.

6. A method according to claim 5, wherein the reference normal population is selected based on at least one of:
    limb dominance;
    differences in limb types;
    ethnicity;
    age;
    gender;
    weight; and,
    height.

7. A method according to claim 5, wherein the at least one reference value is determined based on a linear regression of the first and second dispersion parameter values measured for the reference normal population.

8. A method according to claim 3, wherein the method includes, in the processing system, determining the predicted dispersion parameter value using an equation of the form:

$$DP_p = aDP_2 + K,$$

where:
DP$_2$ is the second dispersion parameter value;
DP$_p$ is the predicted dispersion parameter value;
a is a multiplier reference value determined based on a relationship between the first and second dispersion parameter values in a reference population; and,
K is a constant reference value determined based on the relationship between the first and second dispersion parameter values in the reference population.

9. A method according to claim 8, wherein the first body segment is a leg segment of the subject and the second body segment is an arm segment of the subject, and, for a male subject, the predicted dispersion parameter value for the leg segment based on the second dispersion parameter value for the arm segment is based on:
a value of a in a range 0.15 to 0.022; and,
a value of K in a range 0.62 to 0.72.

10. A method according to claim 8, wherein the first body segment is a leg segment of the subject and the second body segment is an arm segment of the subject, and, for a female subject, the predicted dispersion parameter value for the leg segment based on the second dispersion parameter value for the arm segment is based on:
a value of a in a range 0.44 to 0.41; and,
a value of K in a range 0.43 to 0.46.

11. A method according to claim 3, wherein the method includes, in the processing system, determining the indicator using the equation:

$$Ind = \frac{sf \times (DP_p - DP_1)}{3SE},$$

where:
Ind is the indicator;
DP$_1$ is the first dispersion parameter value determined for the first body segment;
DP$_p$ is the predicted dispersion parameter value for the first body segment;
sf is a scaling factor; and,
SE is a standard error determined based on dispersion parameter values in a reference population.

12. A method according to claim 11, wherein the scaling factor is selected so that a threshold value indicative of the presence or the absence of the oedema is an integer value.

13. A method according to claim 3, wherein the method includes, in the processing system, determining the indicator using the equation:

$$Ind = \frac{sf \times (DP_\mu - DP_1)}{3SE},$$

where:
DP$_\mu$ is a mean dispersion parameter value for a reference normal population;
DP$_1$ is the first dispersion parameter value determined for the first body segment;
sf is a scaling factor; and,
SE is a standard error determined for dispersion parameter values for the reference population.

14. A method according to claim 1, wherein the method includes, in the processing system, determining the indicator based on the equation:

$$Ind = sf(DP_2 - DP_1)$$

where:
Ind is the indicator;
DP$_1$ is the first dispersion parameter value for the first body segment;
DP$_2$ is the second dispersion parameter value for the second body segment; and,
sf is a scaling factor.

15. A method according to claim 1, wherein each dispersion parameter value is indicative of a distribution of the impedance measurements for the respective body segment.

16. A method according to claim 1, wherein the dispersion parameter is based on the value of:

$$\alpha = \frac{2}{\pi} a\tan \frac{(R_0 - R_\infty)}{2|X_c|}.$$

where:
R$_\infty$ = the impedance at infinite applied frequency;
R$_0$ = the impedance at zero applied frequency; and,
X$_c$ = the reactance at the centre of the circle defined by the impedance values.

17. A method according to claim 1, wherein the representation of the indicator includes a linear scale including:
a linear indicator;
a scale; and,
a pointer, the pointer being positioned on the scale in accordance with the indicator.

18. A method according to claim 17, wherein the method includes, in the processing system, displaying the representation including an indication of a change in indicator value from at least one of a previous indicator value and a baseline indicator value.

19. A method according to claim 1, wherein the method includes, in the processing system:
determining at least one threshold using a reference; and,
displaying the at least one threshold as part of the representation.

20. Apparatus for use in diagnosing a presence, absence or degree of oedema in a subject suspected of having the oedema by using impedance measurements performed on the subject, the apparatus including:
a first set of electrodes for applying to the subject;
a signal generator for applying excitation electrical signals to the subject using the first set of electrodes;
a second set of electrodes for applying to the subject;
a sensor for measuring measured electrical signals across the second set of electrodes; and,
a processing system including a processor, a memory, and an I/O device, the processing system for:
causing the impedance measurements to be performed by:
causing the excitation electrical signals to be applied to the subject using the signal generator;
determining the measured electrical signals across the subject using the sensor; and,
determining, using an indication of the excitation electrical signals and an indication of the measured electrical signals, impedance values at each of a number of frequencies for first and second body segments of the subject, each impedance value representing an impedance of the respective body segment, wherein the first body segment is a body segment of the subject that is suspected of being affected by the oedema and the second body segment is a body segment of the subject that is suspected of being unaffected by the oedema;

determining impedance parameter values for the first and second body segments based on the impedance values for the respective body segment, the impedance parameter values including:

$R_\infty$ representing an impedance at infinite applied frequency;

$R_0$ representing an impedance at zero applied frequency; and, $X_c$ representing a reactance at a centre of a circle defined by the impedance values for the respective body segment;

determining first and second dispersion parameter values for the first and second body segments respectively, each dispersion parameter value being indicative of a dispersion of the impedance values for the respective body segment, each dispersion parameter value being based on a ratio of:

a difference between $R_\infty$ and $R_0$ for the respective body segment, and, $X_c$ for the respective body segment;

determining an indicator using the first and the second dispersion parameter values; and, displaying a representation of the indicator, to thereby allow the presence, the absence or the degree of the oedema in the subject to be diagnosed.

21. A method for use in diagnosing a presence, absence or degree of oedema in a subject suspected of having the oedema by using impedance measurements performed on the subject, the method being performed using an apparatus including:

a first set of electrodes for applying to the subject;

a signal generator for applying excitation electrical signals to the subject using the first set of electrodes;

a second set of electrodes for applying to the subject;

a sensor for measuring measured electrical signals across the second set of electrodes; and, a processing system including a processor, a memory, and an I/O device, the method including, in the processing system:

causing the impedance measurements to be performed by:

causing the excitation electrical signals to be applied to the subject using the signal generator;

determining the measured electrical signals across the subject using the sensor; and, determining, using an indication of the excitation electrical signals and an indication of the measured electrical signals, impedance values at each of a number of frequencies for first and second body segments of the subject, each impedance value representing an impedance of the respective body segment, wherein the first body segment is a body segment of the subject that is suspected of being affected by the oedema and the second body segment is a body segment of the subject that is suspected of being unaffected by the oedema;

determining impedance parameter values for the first and second body segments based on the impedance values for the respective body segment, the impedance parameter values including:

$R_\infty$ representing an impedance at infinite applied frequency;

$R_0$ representing an impedance at zero applied frequency; and, $X_c$ representing a reactance at a centre of a circle defined by the impedance values for the respective body segment;

determining first and second dispersion parameter values for the first and second body segments respectively, each dispersion parameter value being indicative of a dispersion of the impedance values for the respective body segment, each dispersion parameter value being based on a ratio of:

a difference between $R_\infty$ and $R_0$ for the respective body segment, and, $X_c$ for the respective body segment;

determining an indicator using the first and the second dispersion parameter values; and, displaying a representation of the indicator, to thereby allow the presence, the absence or the degree of the oedema in the subject to be diagnosed.

* * * * *